United States Patent
Kamenka et al.

(10) Patent No.: US 6,342,511 B1
(45) Date of Patent: Jan. 29, 2002

(54) PHENCYCLIDINE DERIVATIVES, PREPARATION METHOD AND PHARMACEUTICAL COMPOSITIONS CONTAINING SAME

(75) Inventors: Jean-Marc Kamenka, Montpellier; Jacques Hamon, Orsay; Jacques Vignon, Montpellier, all of (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 09/424,884

(22) PCT Filed: Jun. 2, 1998

(86) PCT No.: PCT/FR98/01108

§ 371 Date: Nov. 30, 1999

§ 102(e) Date: Nov. 30, 1999

(87) PCT Pub. No.: WO98/55478

PCT Pub. Date: Dec. 10, 1998

(30) Foreign Application Priority Data

Jun. 3, 1977 (FR) .............................. 97 06777
Jul. 8, 1997 (FR) .............................. 97 08639

(51) Int. Cl.[7] ...................... A61K 31/445; A61K 31/38
(52) U.S. Cl. ...................... 514/326; 514/432; 514/444; 514/447; 546/187; 549/28; 549/60; 549/68

(58) Field of Search .................... 546/187; 514/326, 514/432, 444, 447; 549/68, 28, 60

(56) References Cited

FOREIGN PATENT DOCUMENTS

| EP | 0 31 795 3 | 5/1989 |
|---|---|---|
| EP | 0 40 611 1 | 1/1991 |

OTHER PUBLICATIONS

Hamon et al, Effects . . . Transporter, Euroepan Journal of Medicinal Chemistry, Chimica Therapeutica., vol. 31, No. 6 1996, pp. 489–495.

Kalir et al, "1–Phenylcycloalkylamine Derivatives", Israel Journal of Chemistry, vol. 13, No. 2, 1975 pp. 125–136.

Eiden et al, "Synthese . . . Thia–phencyclidine", vol. 320, No. 4, 1987, Arch. Pharm. , pp. 348–361.

Mousseron et al, "Syntheses . . . phencyclidine" Chimie Therapeutique, vol. 3, No. 4, 1968, pp. 241–247.

*Primary Examiner*—Amelia Owens
(74) *Attorney, Agent, or Firm*—Bierman, Muserlian and Lucas

(57) ABSTRACT

The invention concerns novel phenylcyclidine derivatives with selective affinity for low affinity receptors, methods for preparing them, pharmaceutical compositions containing them and their use as protective agents for central or peripheral nervous system cells against acute or chronic degeneration, or as an anticonvulsant.

15 Claims, No Drawings

PHENCYCLIDINE DERIVATIVES, PREPARATION METHOD AND PHARMACEUTICAL COMPOSITIONS CONTAINING SAME

This application is a 371 of PCT/FR98/01108 filed Jun. 2, 1998.

The [N-(1-phenylcyclohexyl)piperidine (or PCP), developed as an anesthesic agent then withdrawn due to its very significant psychotopic effect, is today no more than a pharmalogical tool, interesting at least through its derivatives or analogues. One of the derivatives, N-(1-(2-thienyl)cyclohexyl)piperidine (or TCP), is, in its tritiated form, a ligand often used as a label for the PCP receptor. In vitro and in vivo studies of the [$^3$H]TCP bond to the PCP receptor has revealed the existence of a second type of bond corresponding to the said PCP sites of low affinity in comparison to the first said sites of high affinity (Brain Res., 378, 133–141 (1986)).

The present invention relates to novel derivatives of phencyclidines with selective affinity for low affinity receptors, processes for their preparation, pharmaceutical compositions containing them and their use as protective agents for central or peripheral nervous system cells against acute or chronic degeneration or as an anticonvulsant.

Therefore the subject of the invention is the compounds of formula I characterized in that they correspond either to formula $I_A$

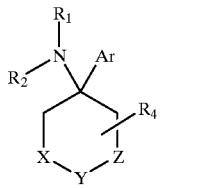

in which

Ar represents a carboxcylic or heterocyclic aryl radical, monocyclic with 5 or 6 members or constituted by condensed rings, and optionally substituted by one or more identical or different radicals chosen from halogen atoms, hydroxyl, alkyl, alkenyl, alkynyl, alkoxy, alkylthio, haloalkyl, hydroxyalkyl radicals, having at most 6 carbon atoms; free esterified or salified carboxy; cyano; nitro; amino optionally substituted by one or two identical or different alkyl radicals containing at most 6 carbon atoms;

$R_1$ and $R_2$ identical or different represent a hydrogen atom or an alkyl radical having at most 6 carbon atoms optionally substituted by one or more identical or different radicals chosen from the hydroxyl, free esterified or salified carboxy, cyano, nitro radicals, or $R_1$ and $R_2$ form with the nitrogen atom to which they are linked a

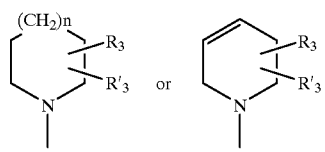

radical in which n represents an integer from 0 to 2 and $R_3$ and $R'_3$ identical or different represent a hydrogen atom, a halogen atom or a hydroxyl, free esterified or salified carboxy, cyano, nitro, alkyl, alkenyl, alkynyl, alkoxy, alkylthio, haloalkyl, hydroxyalkyl radical having at most 6 carbon atoms;

$R_4$ has the same meaning as $R_3$ or $R'_3$;

X, Y and Z are such that at least one represents a sulphur or oxygen atom and the others represent a methylene radical, with the exception of the compounds in which $R_3$, $R'_3$ and R4 each represents a hydrogen atom and 1) $R_1$ and $R_2$ form with the nitrogen atom to which they are linked a pyrrolidine radical, Ar represents a phenyl or 2-thienyl radical and one of X, Y and Z represents an oxygen atom, 2) $R_1$ and $R_2$ form with the nitrogen atom to which they are linked a piperidine radical, Ar represents a phenyl, thienyl and benzothienyl radical, Y represents a sulphur atom and X and Z each represent a methylene radical, 3) $R_1$ and $R_2$ form with the nitrogen atom to which they are linked a piperidine radical, Ar represents a phenyl, methoxyphenyl, benzothienyl or 2-thienyl radical, Y represents an oxygen atom and X and Z each represent a methylene radical, 4) $R_1$ and $R_2$ form with the nitrogen atom to which they are linked a piperidine radical, Ar represents a phenyl, methoxyphenyl or 2-thienyl radical, one of X or Z represents an oxygen atom, the other represents a methylene radical and Y represents a methylene radical, 5) $R_1$ and $R_2$ form with the nitrogen atom to which they are linked a piperidine radical, Ar represents a phenyl or 2-thienyl radical, one of X or Z represents a sulphur atom, the other represents a methylene radical and Y represents a methylene radical, 6) $R_1$ and $R_2$ form with the nitrogen atom to which they are linked a pyrrolidine radical, Ar represents a 2-thienyl radical, one of X or Z represents a sulphur atom, the other represents a methylene radical and Y represents a methylene radical, 7) $R_1$ and $R_2$ form with the nitrogen atom to which they are linked an ethylamino or pyrrolidine radical, Ar represents a phenyl radical, Y represents a sulphur atom and X and Z each represent a methylene radical, or one of the following formulae:
— N-[1-(2-thienyl)-cyclohexan- 1-yl]-3-hydroxymethyl-piperidine,
— N-[1-(2-thienyl)-cyclohexan- 1-yl]-4-hydroxy-3-methyl piperidine,
— N-[1-(2-benzothiophenyl)-cyclohexan-1-yl]-4-hydroxy-3-methyl piperidine,
— N-ethyl-1-(2-thienyl)-cyclohexylamine or
— N-[1-(2-furyl)-cyclohexan-1-yl] piperidine, said compounds of formula I being in all possible racemic, enantiomeric and diastereoisomeric isomer forms as well as the addition salts with mineral and organic acids or with mineral and organic bases of said compounds of formula I.

A more particular subject of the invention is the compounds of general formula IA as defined below in which Ar represents an heterocyclic aryl radical, monocyclic with 5 members or constituted by two condensed rings, and optionally substituted by one or more identical or different alkyl or alkenyl radicals;

$R_1$ and $R_2$, identical or different, represent a hydrogen atom or an alkyl radical having at most 6 carbon atoms or R$_1$ and R$_2$ form together with a nitrogen atom to which they are linked a

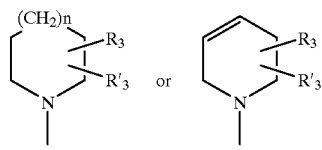

radical in which n is equal to 1 and R$_3$ and R'$_3$, identical or different, represent a hydrogen atom or a hydroxyl. aklyl or hydroxyalkyl radical having at most 6 carbon atoms.

In the definitions indicated above, the expression halogen represents a fluorine, chlorine, bromine or iodine atom.

The expression alkyl having at most 6 carbon atoms represents a linear or branched alkyl radical such as methyl, ethyl, propyl, isopropyl, butyl, isobutyl, sec-butyl, tert-butyl, pentyl, isopentyl, hexyl or isohexyl radical.

Among the alkenyl radicals. The linear or branched alkyl radicals such as vinyl, allyl, 1-propenyl, butenyl, pentynyl or hexynyl radicals can be mentioned.

Among the alkynyl radicals, the ethynyl, propargyl, butynyl, pentynyl or hexynyl radicals can be mentioned. The linear or branched alkoxy radical preferably designates the radicals in which the alkyl radical is as defined above. The methoxy, ethoxy, propoxy, isopropyloxy or butoxy radicals are preferred.

The alkylthio radical preferably designates the radicals in which the alkyl radical is as defined above such as for example methylthio or ethylthio.

The haloalkyl radical preferably designates the radicals in which the alkyl radical is as defined above and is substituted by one or more halogen atoms as defined above such as, for example, bromoethyl, trifluoromethyl, trifluoroethyl or also pentafluoroethyl.

The hydroxyalkyl radical preferably designates the radicals in which the alkyl radical is as defined above such as for example hvdroxymethyl or hydroxyethyl.

The aryl radical can be carbocyclic or heterocyclic. The heterocyclic aryl radical can contain one or more identical or different heteroatoms chosen from oxygen, nitrogen and sulphur atoms. As an example of a carbocyclic or heterocyclic aryl radical, the phenyl. naphthyl, thienyl, furyl, pyridyl, pyrimidyl, pyrrolyl, thiazolyl, diazolyl, oxadiazolyl, benzothienyl, benzofuryl, benzopyrrolyl, benzimidazolyl or indolyl radicals can be mentioned.

A more particular subject of the invention is the compounds of general formula I$_A$ as defined above in which
Ar represents the thienyl, furyl, benzothienyl, benzofuryl radical and optionally substituted by one or more methyl, ethyl, propyl or allyl radicals;
R$_1$ and R$_2$ identical or different represent a hydrogen atom or a methyl or ethyl radical, or
R$_1$ and R$_2$ form with the nitrogen atom to which they are linked a

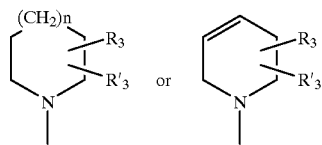

radical in which n is equal to 1 and R$_3$ and R'$_3$ identical or different represent a hydrogen atom or a hydroxyl, hydroxymethyl, hydroxyethyl, methyl or ethyl radical.

More particularly, a subject of the invention is the compounds of formula I$_A$ described hereafter in the examples, in particular the compounds corresponding to the following formulae:

—N-[4-(2-thienyl)-3-methyl-tetrahydro-4H-thiopyran-4-yl]-piperidine;

—N-[4-(2-thienyl)-tetrahydro-4H-thiopyran-4-yl]-3-methyl-piperidine;

—N-[4-(2-benzothiophenyl)-tetrahydro-4H-thiopyran-4-yl]-3-methyl-piperidine;

—N-[4-(2-furyl)-tetrahydro-4H-thiopyran-4-yl]-piperidine;

—N-[4-(2-benzofuranyl)-tetrahydro-4H-thiopyran-4-yl]-piperidine;

—N-[4-(5-methyl-thiophen-2-yl)-tetrahydro-4H-thiopyran-4-yl]-piperidine;

—N-[4-(4-methyl-thiophen-2-yl)-tetrahydro-4H-thiopyran-4-yl]-piperidine;

—N-[4-(2-thienyl)-tetrahydro-4H-thiopyran-4-yl]-3-hydroxy piperidine;

—N-[4-(2-thienyl)-tetrahydro-4H-thiopyran-4-yl]-4-hydroxy piperidine in all the possible racemic, enantiomeric and diastereoisomeric isomer forms as well as the addition salts with mineral and organic acids or with mineral and organic bases of said compounds.

A subject of the invention is also a preparation process for the compounds of general formula I as defined above, characterized in that it comprises the reaction of a compound of formula I

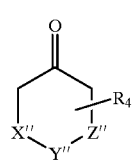

1 in which X", Y", Z" represent a sulphur or oxygen atom or a methylene radical, R$_4$ has the meaning indicated above, with an aryl magnesium halide of formula Ar-Mg-Hal in which Hal represents a halogen atom and Ar has the meaning indicated above, in order to obtain the compound of formula 2

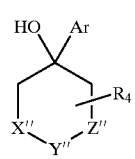

2 in which X", Y", Z", Ar and R$_4$ have the meanings indicated above, the conversion of the hydroxyl radical of the alcohol of formula 2 thus obtained, to an azide of formula 3

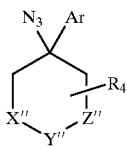

in which X", Y", Z", Ar and R₄ have the meanings indicated above, then the reduction of the acid azide of formula 3 in primary amine of formula 4

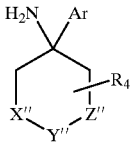

in which X", Y", Z", Ar and R₄ have the meaning indicated above, and finally, if the desired compound of formula I is such that at least one of the $R_1$ or $R_2$ radicals is different from the hydrogen atom or $R_1$ and $R_2$ form a ring with the nitrogen atom to which they are linked, the treatment of this compound of formula 4 in order to obtain the compound of formula I which is converted into the salt if desired.

In this preparation process, the first stage which consists of obtaining the compound of formula 2, is a standard Grignard reaction the implementation conditions of which are known to a person skilled in the art.

The second stage allows access to azide 3 from alcohol 2. The reaction takes place in the presence of an excess of an organic protonating agent such as trichloroacetic acid, an alkaline azide in a polar aprotic solvent. Preferably, the reaction takes place in the presence of an excess of trichloroacidetic acid and sodium azidide in chloroform.

For the reduction of the azides of formula 3 to the primary amine 4, standard methods known to a person skilled in the art for the reduction of azides can be used. The reduction can therefore be carried out using, for example, Raney nickel in isopropanol at 60° C. or lithium aluminium hydride in diethylether or tetrahydrofuran.

If in the desired compound of formula I, $R_1$ and $R_2$ form a ring with the nitrogen atom to which they are linked, the fourth stage is then a cyclization; it is obtained by reacting, in a polar solvent, in an alkaline medium, the compound of formula 4 with the appropriate compound of formula Hal-(CH₂)₂—(CH₂)n-(CH₂)₂-Hal or Hal-(CH₂)—CH=CH—(CH₂)₂-Hal of cis structure, substituted by the $R_3$ and $R'_3$ radicals, and in which n, $R_3$ and $R'_3$ have the meaning indicated above and Hal represents a halogen atom. The alkaline conditions allow the acid formed to be trapped and can be obtained by using, potassium carbonate for example. The polar solvent used can be chosen from methanol, acetone, hexamethylphosphoramide or sulpholane and preferably hexamethylphosphoramide.

The primary amine of formula 4 therefore corresponds to the compound of formula I in which $R_1$ and $R_2$ represent the hydrogen atom. If in the desired compound of formula I, $R_1$ and $R_2$ are identical or different and at least one of the two does not represent the hydrogen atom, then the compound of formula I is a secondary or tertiary amine depending on the values of $R_1$ and $R_2$; these amines can be obtained from the corresponding primary amine of formula 4 according to standard methods known to a person skilled in the art. Thus, for example, for the preparation of the compound of formula I in which one of the $R_1$ or $R_2$ radicals represents the hydrogen atom and the other an alkyl radical, the corresponding primary amine of formula 4 is reacted with the appropriate acid anhydride then the amide obtained is reduced with, for example, LiAlH4.

The different enantiomeric and diastereoisomeric isomer forms can be obtained by resolution either of the starting product or of the final product according to methods known to a person skilled in the art. For example, the two diastereoisomers can be separated in the final stage by simple chromatography. This separation can also be carried out after obtaining the compounds of formula 4. The resolution can also be carried out by using optically active acids such as tartaric or mandelic acids.

A subject of the invention is also another preparation process for the compounds of general formula I as defined above, characterized in that it comprises the reaction of a compound formula 1

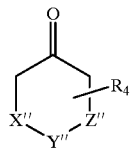

in which X", Y", Z" and R₄ have the meaning indicated above, in an anhydrous medium, with a compound of formula $R_1R_2NH$ in which $R_1$ and $R_2$ have the meanings indicated above, and a cyanide ion donor compound, in order to obtain the compound of formula 5

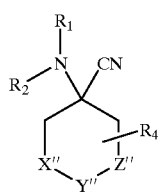

in which X", Y", Z", $R_1$ and $R_2$ have the meanings indicated above, and the reaction of the compound of formula 5 thus obtained, with an aryl magnesium halide of formula Ar-Mg-Hal in which Ar has the meaning indicated above and Hal represents a halogen atom, in order to obtain the compound of formula I according to the invention.

In this second preparation process, the reaction for obtaining the compound of formula 5 can be carried out in the presence of acetone cyanhydrin as cyanide ion doner; as a dehydration agent of the medium, anhydrous magnesium sulphate can for example be used. The reaction is preferably carried out in a polar basic solvent such as acetamide, methylacetamide, dimethylacetamide, acetylpiperidine or piperidine, and preferably dimethylacetamide or piperidine.

The second stage of this second preparation process is a Bruylants reaction (P. Bruylants, Bull. Soc. Chim. Belg., 33, 467 (1924); P. Bruylants, A. Castille, Bull. Soc. Chim. Beig., 34, 261–284 (1925)). On an experimental level, this reaction is stereospecific and leads to the introduction of the aryl radical in equatorial position. As a result, it will only be used for the synthesis of compounds of formula I not possessing a particular stereochemistry.

Taking into account the lack of stereospecificity of this first reaction. this synthesis route is preferentially used in the case where $R_4$ represents a hydrogen atom.

The optional salification of the compounds of formula I is carried out according to the usual methods indicated hereafter in the experimental part.

The starting compounds of formula 1 in which $R_4$ represents the hydrogen atom and Y" represents a sulphur or oxygen atom or a methylene radical, are commercial products. The other starting compounds of formula 1 in which $R_4$ represents the hydrogen atom, can be prepared according to the outline described by T. E. Young (J. Org. Chem., 38, 1562–1566 (1973)). The starting compounds in which $R_4$ is different from the hydrogen atom, can be obtained from the corresponding compounds of formula 1 in which $R_4$ represents the hydrogen atom, according to the substitution methods known to a person skilled in the art.

The compounds of the present invention have a very good affinity and selectivity for a new type of low affinity sites. The action on these sites inhibits the neurotoxicity induced by the glutamate responsible for certain pathological consequences such as acute or chronic degeneration of central or peripheral nervous system cells. The compounds of the present invention can thus be used in different therapeutic applications.

Thus the compounds of the present invention can be used to protect the central or peripherial nervous system cells against acute degeneration induced by accidents such as trauma, ischemia or the action of endogenic and exogenic neurotoxic agents, directly or by means of secondary mechanisms.

The compounds can also be used to protect the central or peripherial nervous system cells against chronic degeneration induced by neurodegenerative diseases and processes of pathological aging type, dementia, Alzheimer's disease, Parkinson's disease, amyotrophic lateral sclerosis. They can also be used as anticonvulsants or antidepressants or to stimulate alertness, to treat states of dependency on different substances such as addictive drugs.

An illustration of the pharmacological properties of the compounds of the invention will be found hereafter in the experimental part.

These properties make the compounds of formula I suitable for pharmaceutical use. A subject of the present Application is, as medicaments, the compounds of formula I as defined above, in all possible racemic, enantiomeric and diastereoisomeric isomer forms, as well as the addition salts with pharmaceutically acceptable mineral or organic acids or mineral or organic bases of said compounds of formula I, as well as the pharmaceutical compositions containing, as active ingredient, at least one of the medicaments as defined above.

The invention thus relates to the pharmaceutical compositions containing a compound of the invention or an addition salt of a pharmaceutically acceptable acid or base of the latter, in combination with a pharmaceutically acceptable support. The pharmaceutical composition can be in the form of a solid, for example, powders, granules, tablets, gelatin capsules or suppositories. The appropriate solid supports can, for example, be calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound according to the invention can also be presented in liquid form, for example, solutions, emulsions, suspensions or syrups. The appropriate liquid supports can be, for example, water, organic solvents such as glycerol or glycols, similarly their mixtures, in varied proportions, in water, with pharmaceutically acceptable oils or greases added to them. Sterile liquid compositions can be used for intramuscular or sub-cutaneous injections and the sterile compositions can also be administered intravenously. The compositions according to the invention can also be administered by other standard routes such as oral administration.

A subject of the invention is also the use of the compounds of formula I' characterized in that they correspond either to formula I'A

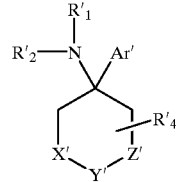

in which

Ar' represents a carbocyclic or heterocyclic aryl radical, monocyclic with 5 or 6 members or constituted by condensed rings and optionally substituted by one or more identical or different radicals chosen from the halogen atoms, the hydroxyl, alkyl, alkenyl, alkynyl, alkoxy, alkylthio, haloalkyl, hydroxyalkyl radicals, having at most 6 carbon atoms; free esterifed or salified carboxy; cyano; nitro; amino optionally substituted by one or two identical or different alkyl radicals containing at most 6 carbon atoms;

$R'_1$ and $R'_2$ identical or different represent a hydrogen atom or an alkyl radical having at most 6 carbon atoms optionally substituted by one or more identical or different radicals chosen from the hydroxyl, free esterified or salified carboxy, cyano, nitro radicals or $R'_1$ and $R'_2$ form with the nitrogen atom to which they are linked a

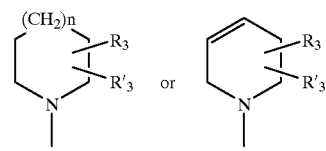

radical in which n represents an integer from 0 to 2 and $R_3$ and $R'_3$ identical or different represent a hydrogen atom, a halogen atom or a hydroxyl, free esterified or salified carboxy, cyano, nitro, alkyl, alkenyl, alkynyl, alkoxy, alkylthio, haloalkyl, hydroxyalkyl radical having at most 6 carbon atoms;

$R'_4$ has the same meaning as $R_3$ or $R'_3$;

X', Y' and Z' are such that at least one represents a sulphur or oxygen atom or a methylene radical and the others represent a methylene radical, or one of the following formulae:

—N- [1-(2-thienyl)-cyclohexan-1-yl]-3-hydroxymethyl-piperidine,

—N-[1-(2-thienyl)-cyclohexan-1-yl]-4-hydroxy-3-methyl piperidine,

—N-[1-(2-benzothiophenyl)-cyclohexan-1-yl]-4-hydroxy-3-methyl piperidine or

—N-ethyl-1-(2-thienyl)-cyclohexylamine,

—N-[1-(2-furyl)-cyclohexan-1-yl] piperidine,

—N-[1-(2-thienyl)-cyclohexan-1-yl]-3-methyl-piperidine, said compounds of formula I' being in all possible racemic, enantiomeric and diastereoisomeric isomer forms as well as the use of addition salts with mineral and organic acids or with mineral and organic bases of said compounds of formula I', for the preparation of medicaments intended to protect the central or peripherial nervous system cells against acute degeneration induced by accidents such as trauma, ischemia or the action of endogenous or exogenous neurotoxic agents, directly or by means of secondary mechanisms.

The invention also relates to the use of the compounds of formula I' as defined above, for the preparation of medicaments intended to protect the central or peripherial nervous system cells against chronic degeneration induced by neurodegenerative processes or diseases of pathological aging type, dementia, Alzheimer's disease, Parkinson's disease, amyotrophic sclerosis, as well as anticonvulsants or antidepressant medicaments or medicaments to stimulate alertness, to treat states of dependancy on different substances such as addictive drugs like cocaine.

The invention more particularly relates to the use of compounds of formula I'$_A$ as defined above in which Ar' represents a heterocyclic aryl radical, monocyclic with 5 members or constituted by two condensed rings and optionally substituted by one or more identical or different alkyl or alkenyl radicals;

R'$_1$ and R'$_2$ identical or different represent a hydrogen atom or an alkyl radical having at most 6 carbon atoms or R$_1$ and R$_2$ form with the nitrogen atom to which they are linked a

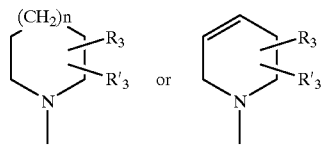

radical in which n is equal to 1 and R$_3$ and R'$_3$ identical or different represent a hydrogen atom or a hydroxyl, alkyl or hydroxyalkyl radical having at most 6 carbon atoms, for the preparation of medicaments as defined above.

The invention also relates more particularly to the use of the compounds of formula I'A as defined above in which Ar' represents the thienyl, furyl, benzothienyl, benzofuryl radical and optionally substituted by one or more methyl, ethyl, propyl or allyl radicals;

R'$_1$ and R'$_2$, identical or different, represent a hydrogen atom or a methyl or ethyl radical, or R$_1$ and R$_2$ form with the nitrogen atom to which they are linked a

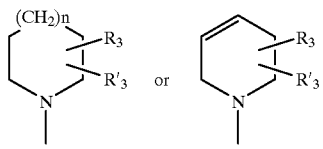

radical in which n is equal to 1 and R$_3$ and R'3, identical or different, represent a hydrogen atom or a hydroxyl, hydroxymethyl, hydroxyethyl, methyl or ethyl radical, for the preparation of medicaments as defined above.

More particularly, a subject of the invention is the use of compounds of formula I'A and corresponding to the following formulae:

—N-[4-(2-thienyl)-3-methyl-tetrahydro-4H-thiopyran-4-yl]-piperidine;

—N-[4-(2-thienyl)-tetrahydro-4H-thiopyran-4-yl]-3-methyl-piperidine;

—N-[4-(2-benzothiophenyl)-tetrahydro-4H-thiopyran-4-yl]-3-methyl-piperidine;

—N-[4-(2-furyl)-tetrahydro-4H-thiopyran-4-yl]-piperidine;

—N-[4-(2-benzofuranyl)-tetrahydro-4H-thiopyran-4-yl]-piperidine;

—N-[4-(5-methyl-thiophen-2-yl)-tetrahydro-4H-thiopyran-4-yl]-piperidine;

—N-[4-(4-methyl-thiophen-2-yl)-tetrahydro-4H-thiopyran-4-yl]-piperidine;

—N-[4-(2-thienyl)-tetrahydro-4H-thiopyran-4-yl]1-3-hydroxy piperidine;

—N-[4-(2-thienyl)-tetrahydro-4H-thiopyran-4-yl]-4-hydroxy piperidine;

—N-[4-(2-thienyl)-tetrahydro-4H-thiopyran-4-yl] piperidine;

—N-[4-(2-thienyl)-tetrahydro-4H-pyran-4-yl] piperidine;

—N-[3-(2-thienyl)-tetrahydro-4H-thiopyran-3-yl] piperidine;

for the preparation of medicaments as defined above.

The following examples are presented in order to illustrate the above procedures and must in no case be considered as a limit to the scope of the invention.

EXPERIMENTAL PART

Example 1

N-[4-(2-thienyl)-3-methyl-tetrahydro-4H-thiopyran-4-yl] piperidine

Stage 1a: 3-methyl-tetrahydro-4H-thiopyran-4-one

Diisopropylamine (8.4 ml, 60 mmole) and 74 ml of THF are introduced under nitrogen into a 250 ml three-necked flask. nBuLi (37.5 ml, 60 mmole) is introduced dropwise and agitated for an additional half-hour at 25° C. The lithium diisopropylamide solution (0.5 M) obtained is cooled down to −80° C. Tetrahydro-4H-thiopyran-4-one (6.96 g, 60 mmole) is added slowly. After half an hour, methyl iodide (5.6 ml, 90 mmole) is added and the temperature is allowed to return to 25° C. After five hours of agitation, a salt saturated solution of sodium bicarbonate (5%) is added, followed by decanting, the organic phase is dried over sodium sulphate and concentrated to dryness. The orange oil obtained is chromatographed on silica eluting with an EP/AcOEt 90/10 mixture. In this way, a colourless oil is obtained (3.2 g).

NMR $^1$H: 2.8 (m, 3H); 2.4 (m, 4H); 0.95 (d, 3H, J=6.1 Hz).

NMR $^{13}$C: 209.52 (C4); 47.20 (C3); 43.45 (C5); 30.07 (C2); 30.38 (C6); 14.41 (CH$_3$)

Stage 1. b: 4-(2-thienyl)-3-methyl-tetrahydro-4H-thiopyran-4-ols 2-thienylmagnesium bromide is prepared under nitrogen from magnesium (0.9 g, 37.2 mmole), 2-bromo-thiophene (6.1 g, 37.2 mmole) and 100 ml of anhydrous ether followed by heating at 45° C. for 3 hours, then 3-methyl-tetrahydro-4H-thiopyran-4-one (4.2 g, 33 mmole) dissolved in ether (50 ml) is added at ambient temperature. The reaction medium is heated for 16 hours under reflux. After cooling down, the reaction medium is poured into 100 ml of an aqueous solution saturated in NH4Cl, followed by agitation for 30 minutes in order to destroy the magnesium complex. After decanting, the aqueous phase is extracted with ether (3×50 ml) which is then neutralised by NH4OH (25%). After extraction with ether (3×50 ml), the combined organic phases are washed with water to neutrality, dried over Na$_2$SO$_4$, filtered and concentrated to dryness. The green oil obtained (7.6 g) is chromatographed on silica eluting with an EP/EA (90/10) mixture. A limpid oil is thus obtained.

Rf (silica, eluent EP/EA 60/40): 0.4

GC/MS (90–250° C. (10° C./min)):

Tr=14.40 min (majority diastereoisomer: 87%)

Tr=14.71 min (minority diastereoisomer: 13%)

NMR $^{13}$C: majority diastereoisomer: 153.65 (C2'); 126.88–121.80 (C3' to C5'); 74.52 (C4); 43.33 (C5); 42.68 (C3); 30.67 (C2); 23.89 (C6); 15.86 (CH$_3$). minority diastereoisomer: 153.0 (C2'); 126.43–122.98 (C3' to C5'); 73.33 (C4); 40.25 (C3); 33.84 (C5); 30.17 (C2); 23.89 (C6); 15.04 (CH$_3$).

Stage 1. c: 4-(2-thienyl)-3-methyl-tetrahydro-4H-thiopyran-4-yl-azides

Trichloracetic acid (15.1 g, 92.4 mmole) is dissolved in chloroform (100 ml). Sodium azide (4 g, 61.7 mmole) is added and the medium is cooled down to 10° C. The diastereoisomer alcohols obtained according to the previous stage (6.6 g, 30.8 mmole) dissolved in chloroform (50 ml) are added dropwise. The reaction medium is agitated for 72 hours whilst maintaining the temperature at 10–12° C. A solution of ammonium hydroxide (10%) is then added until neutralisation, then the aqueous phase is extracted with dichloromethane (3×100 ml). The organic phase is washed with water (200 ml), dried over Na$_2$SO$_4$ and concentrated to dryness. In this way, a brown oil is obtained (6.8 g) which is then used without further purification.

Rf (silica, eluent EP/EA 60/40): 0.37

GC/MS (60–250° C.(10° C./min)):

Tr=18.31 min (majority diastereoisomer: 72%)

Tr=18.08 min (minor diastereoisomer: 28%)

Stage 1. d: 4-(2-thienyl)-3-methyl-tetrahydro-4H-thiopyran-4-yl-amines

Lithium aluminium hydride (0.87 g, 23 mmole) in THF is introduced into a 100 ml three-necked flask at 0° C. The azide mixture obtained in the previous stage (5.5 g, 23 mmole) dissolved in 30 ml of THF is added dropwise. The reaction medium is agitated for 24 hours at ambient temperature. The minimum amount of ammonium hydroxide (10%) is added very slowly in order to destroy the excess LiAlH$_4$, followed by filtering on celite, the precipitate is washed with dichloromethane (300 ml) and concentrated to dryness. The brown oil obtained is taken up in ether and extracted with a solution of HCl (10%) (3×100 ml). The aqueous phase is then neutralised with ammonium hydroxide (20%) and extracted with ether (3×100 ml). The organic phase is washed with water, dried over MgSO$_4$ and concentrated to dryness. The product obtained is purified by chromatography on silica eluting with an EP/EA 50/50 mixture. In this way, a colourless oil is obtained (3.7 g).

Rf (silica, eluent EP/EA 60/40): 0.20 (majority) and 0.25 (minority)

GC/MS (90–250° C. (10° C./min)):

Tr=24.15 min (majority diastereoisomer: 62.5%)

Tr=23.77 min (minority diastereoisomer: 37.5%)

NMR $^{13}$C (majority): 155.11 (C2'); 125.99–121.94 (C3' to C5'); 54.80 (C4); 40.72 (C3); 34.51 (C5); 30.66 (C2); 23.44 (C6); 15.34 (CH$_3$). NMR $^{13}$C (minority): 156.60 (C2'); 126.41–121.26 (C3' to C5'); 55.84 (C4); 43.92 (C5); 42.40 (C3); 30.04 (C2); 23.35 (C6); 15.97 (CH$_3$).

Stage 1. e: N-[4-(2-thienyl)-3-methyl-tetrahydro-4H-thiopyran-4-yl] piperidines

The amine mixture of Stage 1d above (4.5 g, 21 mmoles) is dissolved in HMPT (50 ml). Potassium carbonate (5.8 g, 42 mmoles) and 1,5-dibromopentane (3.6 ml, 26.2 mmoles) are added. The medium is agitated under nitrogen at 60° C. for 48 hours. After cooling down, this solution is poured into water (200 ml) and extracted with ether (3×100 ml). As previously, an acid-base washing is carried out, followed by re-extraction with ether, the ethereal phase is washed with water, followed by drying over magnesium sulphate and concentration to dryness. The yellow oil obtained (6.2 g) is purified by chromatography on silica eluting with an EP/EA (90/10) mixture. In this way, the two diastereoisomers are obtained separately: the majority diastereoisomer (2 g, 34%) and the minority diastereoisomer (0.7 g, 12%), both in the form of a white solid.

Rf (silica, eluent EP/AP 90/10): 0.6 (trans), 0.4 (cis)

CPV:

Tr (majority)=18.15 min and Tr (racemic)=19.75 min

Tr (minority)=18.46 min and Tr (racemic)=18.95 min

NMR $^{13}$C (majority): 145.88 (C2'); 125.80–122.41 (C3' to C5'); 61.51 (C4); 45.96 (Cα); 33.26 (C3); 29.47 (C5); 28.38 (C2); 26.90 (Cβ); 25.03 (C6); 22.93 (Cγ); 15.10 NMR $^{13}$C (minority): 142.70 (C2'); 126.23–122.76 (C3' to C5'); 62.08 (C4); 45.59 (Cα); 33.55 (C3); 32.88 (C5); 30.64 (C2); 26.87 (Cβ); 25.38 (C6); 25.03 (Cγ); 13.41 (CH$_3$).

Example 2

(±)-N-[4-(2-thienyl)-tetrahydro-4H-thiopyran-4-yl]-3-methyl-piperidine

Stage 2a: 4-(3-methyl-piperidino)-tetrahydro-4H-thiopyran-4-carbonitrile

Magnesium sulphate (9.6 g, 80 mmoles), DMA (2 g, 23 mmoles), (±)-3-methylpiperidine (4 g, 40 mmoles), tetrahydro-4H-thiopyran-4-one (2.3 g, 20 mmoles) and acetone cyanohydrin (1.7 g, 20 mmoles) are introduced in succession into a 250 ml two-necked flask. The reaction medium is agitated for 48 hours at 45° C. After cooling down to ambient temperature, the pasty mixture obtained is placed on ice (approximately 150) and agitated for 30 minutes. Extraction with ether is then carried out (3×80 ml), the combined organic phases are washed with water (100 ml), followed by drying over Na$_2$SO$_4$, filtering and concentration to dryness. A brown oil is thus obtained (4.5 g, 20 mmoles) constituted by a mixture of expected product with approximately 4% of amino nitrite originating from acetone and 7% of the remaining tetrahydro-4H-thiopyran-4-one. The product is then used without further purification.

NMR $^{13}$C: 118.3 (CN); 59.43(C4); 54.1 (Cα); 46.42 (Cα'); 34.3 (C3*); 34.2 (C5*); 32.1 (Cγ); 30.9; 25.1 (C2–C6); 22.8 (Cβ'); 19.3 (CH$_3$).

Stage 2b: (±)-N-[4-(2-thienyl)-tetrahydro-4H-thiopyran-4-yl]-3-methyl-piperidine 2-thienylmagnesium bromide is prepared under nitrogen from magnesium turnings (1 g, 40 mmoles), 2-bromothiophene (6.52 g, 40 mmoles) and 150 ml of anhydrous ether. The ether is heated under reflux for 3 hours then the aminonitrile obtained according to the previous stage (2.25 g, 10 mmoles) is added at ambient temperature. The reaction medium is heated for 20 hours under reflux. After the usual treatment, a brown oil is obtained which is chromatographed on 100 g of alumina eluting with an EP/EA (95/5) mixture. In this way, a colourless oil is obtained (1.6 g).

NMR $^{13}$C: 146.6 (C2'); 126,0–122.7 (C3' to C5'); 58.2 (C4); 53.35 (Cα); 45.5 (Cα'); 37.1 (C3*); 36.8 (C5*); 33.2 (Cβ'); 31.8 (Cβ); 23.4 (C2–C6); 22.5 (Cγ); 19.3 (CH$_3$).

The corresponding hydrochloride is prepared by treatment of the base in hydrochloric ether for 3 hours. After filtration and abundant rinsing with anhydrous ether, a white powder is obtained (1.42 g). M.p.=168° C.

NMR $^{13}$C: 134.5 (C2'); 130,3–127.9 (C3' to C5'); 68.9 (C4); 52.3 (Cα); 46.2 (Cα') 33.4 (C3*); 33.2 (C5*); 30.5 (Cβ'); 28.2 (Cβ); 24.9 (C2–C6); 22.1 (Cγ); 18.9 (CH$_3$).

Example 3

S-(−)-N-[4-(2-thienyl)-tetrahydro-4H-thiopyran-4-yl]-3-methyl-piperidine

Stage 3a: S-(+)-3-methyl-piperidine (+) mandelic acid (45.64 g, 0.3 mol) is dissolved in 300 ml of warm ethyl acetate. 3-methylpiperidine (29.8 g, 0.3 mol) is added under agitation and the solution allowed to return to ambient temperature. After 24 hours, the salt obtained is filtered and rinsed with an EA/AcOEt (1/1) mixture then recrystallized 3 times from AcOEt. In this way, the (S)-(+)-3-methylpiperidine mandelate salt (22.7 g) is obtained. M.p.=120–122° C; αD=+58.0° (methanol, c=1.0).

These crystals are taken up in 50 ml of an aqueous solution of soda at 25% then the solution is extracted with ether (3×50 ml). The combined organic phases are washed with a saturated solution of NaCl, dried over MgSO$_4$, then concentrated. The oil obtained is distilled to atmospheric pressure in order to produce a colourless liquid (7.1 g). M.p.=92–97° C.

NMR $^{13}$C=53.2 (C2); 45.1 (C6); 32.2 (C4); 30.6 (C3); 25.2 (C5); 18.0 (CH$_3$).

Stage 3b: S-4-(3-methyl-piperidino)-tetrahydro-4H-thiopyran-4-carbonitrile

The operating method is identical to that illustrated in Stage 2a using S-(−)-3-methylpiperidine instead of (±)-3-methylpiperidine. Stage 3c: S-(−)-N-[4-(2-thienyl)-tetrahydro-4H-thiopyran-4-yl]-3-methyl-piperidine The operating method is identical to that illustrated in Stage 2b using S-4-(3-methyl-piperidino)-tetrahydro-4H-thiopyran-4-carbonitrile instead of (±)-4-(3-methyl-piperidino)-tetrahydro-4H-thiopyran-4-carbonitrile. A colourless oil is obtained (1.8 g) which crystallizes when cold. M.p.=53–55° C.

The hydrochloride is obtained according to the operating method described in Stage 2b.

M.p.=169–171° C. αD=−10° (methanol, c=1.0)

Example 4

R-(+)-N-[4-(2-thienyl)-tetrahydro-4H-thiopyran-4-yl]-3-methyl-piperidine

Stage 4a: R-(−)-3-methyl-piperidine

The crystallization and recrystallization filtrates of the S-(+)-3-methyl-piperidine mandelic salts from the previous Stage 3a are recombined and treated with 100 ml of an aqueous solution of soda (25%). After 30 minutes under agitation, this aqueous phase is extracted with ether (4×50 ml). The combined organic phases are washed with a saturated solution of NaCl (100 ml), dried over MgSO4, then concentrated. In this way, a liquid enriched in (R)-(+)-3-methylpiperidine is obtained which is added to 30 g of (−) mandelic acid dissolved in 180 ml of warm ethyl acetate. After 24 hours, the salt obtained is filtered and rinsed with an EA/AcOEt (1/1) mixture then recrystallized twice from ethyl acetate. The R-(−)-3-methyl-piperidine mandelate salt is obtained in the form of white crystals (17 g).

M.p.=121–123° C.; αD=−56.5° (methanol, c=1.0)

These crystals are taken up in 50 ml of a 25% aqueous soda solution then the solution is extracted with ether (3–50 ml). The combined organic phases are washed with a saturated solution of NaCl, dried over MgSO$_4$, then concentrated. The oil obtained is distilled at atmospheric pressure in order to produce a colourless liquid (5.2 g).

Stage 4b: R-4-(3-methyl-piperidino)-tetrahydro-4H-thiopyran-4-carbonitrile

The operating method is identical to that illustrated in Stage 2a, using R-(+)-3-methylpiperidine instead of (±)-3-methylpiperidine.

Stage 4c: R-(+)-N-[4-(2-thienyl)-tetrahydro-4H-thiopyran-4-yl]-3-methyl-piperidine The operating method is identical to that illustrated in Stage 2b, using R-4-(3-methyl-piperidino)-tetrahydro-4H-thiopyran-4-carbonitrile instead of (±)-4-(3-methyl-piperidino)-tetrahydro-4H-thiopyran-4-carbonitrile. A colourless oil is obtained (1.65 g) which crystallizes when cold. M.p.=54–56° C.

The hydrochloride is obtained according to the operating method described in Stage 2b.

M.p.=170–172° C. αD=+12° (methanol, c=1.0)

Example 5

(±)-N-[4-(2-benzothiophenyl)-tetrahydro-4H-thiopyran-4-yl]-3-methyl-piperidine 4-(3-methyl-piperidino)-tetrahydro-4H-thiopyran-4-carbonitrile (2 g, 8.9 mmoles) dissolved in 50 ml of anhydrous ether is introduced dropwise into a 2-benzothiophenylmagnesium bromide (44.7 mmoles) solution. Ether is heated under reflux for 20 hours. After the usual treatment, a brown oil is obtained (1.7 g) which is chromatographed on 60 g of alumina eluting with an EP/EA (95/5) mixture. In this way, a white solid is obtained (1.2 g, 40%).

M.p.=90–92° C. NMR $^{13}$C: 147.99 (C2'); 139.19 (C7'a); 138.32 (C3'a); 123.90 to 119.96 (C3' to C7') 58.88 (C4); 53.45 (Cα); 45.65 (Cα'); 36.78 (C3*); 36.52 (C5*); 33.17 (Cβ'); 31.85 (Cβ); 26.14 (Cγ); 23.52 (C2–C6); 19.77 (CH$_3$).

The corresponding hydrochloride is prepared. M.p.=160° C.

NMR $^{13}$C: 139.45 (C2'); 138.63 (C7'a); 135.04 (C3'a); 127.89 to 121.86 (C3' to C7'); 69.26 (C4); 52.75 (Cα); 46.72 (Cα'); 33.48 (C3*); 33.29 (C5*); 30.57 (Cβ'); 28.41 (Cβ); 25.06 (C2–C6); 22.21 (Cγ); 18.92 (CH$_3$).

Example 6

R-(+)-N-[4-(2-benzothiophenyl)-tetrahydro-4H-thiopyran-4-yl]-3-methyl-piperidine The operating method is identical to that of Example 5 using R-4-(3-methyl-piperidino)-tetrahydro-4H-thiopyran- 4-carbonitrile instead of 4-(3-methyl-piperidino)-tetrahydro-4H-thiopyran-4-carbonitrile. The same quantites of reagents are used. Colourless crystals are obtained (1.85 g).M.p.=90–92° C.

Characteristics of the corresponding hydrochloride:
M.p.=158–165° C.; αD=+27.2° (methanol, c=1.0)

Example 7

S-(–)-N-[4-(2-benzothiophenyl)-tetrahydro-4H-thiopyran-4-yl]-3-methyl-piperidine The operating method is identical to that in Example 5 using S-4-(3-methyl-piperidino)-tetrahydro-4H-thiopyran-4-carbonitrile instead of 4-(3-methyl-piperidino)-tetrahydro-4H-thiopyran-4-carbonitrile. The same quantites of reagents are used. Colourless crystals are obtained (1.2 g).M.p.=91–93° C.

Characteristics of the corresponding hydrochloride:
M.p.=162–168° C.; αD=–23.6° (methanol, c=1.0).

Example 8

N-[1-(2-thienyl)-cyclohexan-1-yl]-3-hydroxymethyl-piperidine

Stage 8a: 1-[1-(3-hydroxymethyl-piperidino)-cyclohexan-1-yl]-carbonitrile

It is prepared from $MgSO_4$ (9 g, 75 mmoles), (2.2 g, 25 mmoles), 3-hydroxymethyl-piperidine (5.8 g, 38 mmoles), cyclohexanone (2.5 g, 25 mmoles) and acetone cyanohydrin (2.2 g, 25 mmoles) as described previously in Stage 2a. After treatment of the reaction, a white solid is obtained (4.5 g).

NMR $^{13}$C: 118.89 (CN); 64.94 (CH2OH); 60.93 (C1); 50.17 (Cα); 47.07 (Cα'); 34.75 (Cβ); 33.72 (C2*); 33.60 (C6*); 26.79 (Cγ); 24.65 (C3–C5); 21.83 (C4).

Stage 8b: N-[1-(2-thienyl)-cyclohexan-1-yl]-3-hydroxymethyl-piperidine 2-thienylmagnesium bromide is prepared under nitrogen from magnesium (0.66, 27.2 mmoles), 2-bromothiophene (4.4 g, 9.5 mmoles) and 80 ml of anhydrous ether followed by heating at 45° C. for 3 hours, then 1-[1-(3-hydroxymethyl-piperidino)-cyclohexan-1-yl]-carbonitrile (2 g, 9 mmoles) dissolved in ether is added at ambient temperature. The reaction medium is heated for 20 hours under reflux. After treatment of the reaction, 2.1 g of a yellow oil is obtained which is chromatographed on alumina eluting with an EP/EA (50/50) mixture. In this way, a colourless oil is obtained (1.4 g).

NMR $^{13}$C: 145.45 (C2'); 125.84 to 122.76 (C3' to C5'); 66.66 (CH$_2$OH); 60.06 (C1); 49.26 (Cα); 46.08 (Cα'); 38.44 (Cβ); 35.89 (C2*); 35.69 (C6*); 27.73 (Cβ'); 25.22 (Cγ); 24.70 (C3–C5); 22.08 (C4).

Characteristics of the corresponding hydrochloride:
M.p.=176–178° C. NMR $^{13}$C: 135.76 (C2'); 130.57 to 127.92 (C3' to C5'); 69.74 (CH2OH); 64.20 (C1); 49.69 (Cα); 46.85 (Cα'); 36.60 (Cβ); 33.37 (C2*); 33.00 (C6*); 25.27 (Cβ'); 23.97 (Cγ); 23.03 (C3–C5); 22.21 (C4).

Example 9

N-[4-(2-furyl)-tetrahydro-4H-thiopyran-4-yl]-piperidine

Stage 9a: 4-piperidino-tetrahydro-4H-thiopyran-4-carbonitrile

Magnesium sulphate (9.3 g, 77.4 mmoles), DMA (2.25 g, 25.8 mmoles), piperidine (4.4 g, 51.6 mmoles), tetrahydro-4H-thiopyran-4-one (3 g, 25.8 mmoles) and acetone cyanhydrin (2.2 g, 25.8 mmoles) are introduced in succession into a 250 ml two-necked flask. The reaction medium is agitated for 48 hours at 45° C.

After cooling down to ambient temperature, the mixture obtained is placed on ice (approximately 100 g) and agitated for 30 minutes. Extraction with ether (3×80 ml) is then carried out, the combined organic phases are washed with water (100 ml), dried over $Na_2SO_4$, filtered and concentrated to dryness. An orange oil is obtained (5.3 g, 25.2 mmoles) which is then used without particular purification.

NMR $^{13}$C: 118.34 (CN); 59.61 (C4); 46.985 (Cα); 34.215 (C3–C5); 25.72 (C2–C6); 23.77 (Cβ); 22.76 (Cγ).

Stage 9b: N-[4-(2-furyl)-tetrahydro-4H-thiopyran-4-yl]-piperidine

An $MgBr_2$ solution is prepared by adding 1,2-dibromo-ethane (6.76 g, 36 mmoles) diluted in 80 ml of anhydrous ether to magnesium turnings (0.88 g, 36 mmoles) dropwise and under nitrogen. The solution is maintained at ambient temperature for 2 hours.

A 2-lithio-furan solution is prepared simultaneously at –20° C. and under nitrogen by adding a 1.6 M solution of n-butyllithium in hexane (28 ml, 45 mmoles) dropwise to a furan mixture (3.1 g, 45 mmoles). This mixture is heated for 2 hours under reflux.

This solution is decanted at ambient temperature. The aminonitrile of Stage 9a (1.9 g, 9 mmoles) dissolved in 50 ml of anhydrous ether is added dropwise to the 2-furylmagnesium bromide solution. The ether is heated under reflux for 16 hours. After the usual treatment, a brown solid is obtained (1.8 g) which is chromatographed on 60 g of aluminium eluting with an EP/EA (98/2) mixture. In this way, a white solid is obtained (1.6 g, 71%).

M.p.=79–81° C. NMR $^{13}$C: 156.49 (C2'); 141.05 (C5'); 109.27 (C3'); 106.10 (C4'); 57.47 (C4); 46.44 (Cα); 33.57 (C3–C5); 26.58 (C2–C6); 24.55 (Cγ); 23.30 (Cβ).

Characteristics of the corresponding hydrochloride:
M.p.=171–173° C. NMR $^{13}$C: 145.25 (C2'); 143.49 (C5'); 113.71 (C3'); 110.74 (C4'); 66.84 (C4); 46.74 (Cα); 30.25 (C3–C5); 24.52 (C2–C6); 21.96 (Cβ); 21.33 (Cγ).

Example 10

N-[4-(2-benzofuryl)-tetrahydro-4H-thiopyran-4-yl]-piperidine

The preparation process is identical to that in Stage 9b but using a 2-lithio-benzofuran solution instead of a 2-lithio-furan solution.

After the usual treatment, a yellow solid is obtained which is chromatographed on alumina eluting with an EP/EA (98/2) mixture. In this way, a white solid is obtained (67%).

M.p.=109–111° C. NMR $^{13}$C: 159.78 (C2'); 154.0 (C7'a); 127.83 (C3'a); 123.42 to 102.8 (C3' to c7'); 57.76 (C4); 46.62 (Cα); 33.78 (C3–C5); 26.81 (C2–C6); 24.64 (Cγ); 23.17 (Cβ).

Characteristics of the corresponding hydrochloride:
M.p.=171–173° C. NMR $^{13}$C: 154.18 (C2'); 147.88 (C7'a); 126.65 (C3'a); 125.80 to 111.07 (C3' to C7'); 67.83 (C4); 47.55 (Cα); 30.77 (C3–C5); 24.99 (C2–C6); 22.47 (Cβ); 24.64 (Cγ).

Example 11

N-[4-(5-methyl-thiophen-2-yl)-tetrahydro-4H-thiopyran-4-yl]-piperidine

The preparation process is identical to that of Stage 9b but using a 2-lithio-5-methyl-thiophene solution instead of a 2-lithio-furan solution.

After the usual treatment, a yellow solid is obtained which is chromatographed on alumina eluting with an EP/EA (98/2) mixture. In this way, a white solid is obtained (67%).

M.p.=93–95° C. NMR $^{13}$C: 144.04 (C2'); 136.95 (C5'); 124.05 (C3'); 123.05 (C4'); 58.44 (C4); 45.96 (Cα); 36.65 (C3–C5); 26.74 (C2–C6); 24.88 (Cγ); 23.37 (Cβ); 15.09 (CH$_3$).

Characteristics of the corresponding hydrochloride:

M.p.=160–162° C. NMR $^{13}$C: 142.88 (C2'); 131.34 (C5'); 130.25 (C3'); 125.82 (C4'); 68.83 (C4); 46.47 (Cα); 32.89 (C3–C5); 24.68 (C2–C6); 22.27 (Cβ); 21.69 (Cγ); 14.75 (CH$_3$).

Example 12

N-[4-(4-methyl-thiophen-2-yl)-tetrahydro-4H-thiopyran-4-yl]-piperidine

The preparation process is identical to that of Stage 9b but using a 2-lithio-4-methyl-thiophene solution instead of a 2-lithio-furan solution.

After the usual treatment, a brown solid is obtained which is chromatographed on alumina eluting with an EP/EA (90/10) mixture. In this way, a white solid is obtained (55%).

M.p.=89–91° C. NMR $^{13}$C: 146.04 (C2'); 136.32 (C4'); 125.63 (C3'); 118.05 (C5'); 58.34 (C4); 45.95 (Cα); 36.66 (C3–C5); 26.74 (C2–C6); 24.68 (Cγ); 23.32 (Cβ); 15.78 (CH$_3$).

Characteristics of the corresponding hydrochloride:

M.p.=144–146° C. NMR $^{13}$C: 138.86 (C2'); 134.17 (C5'); 132.68 (C3'); 123.93 (C4'); 69.43 (C4); 47.17 (Cα); 33.57 (C3–C5); 25.21 (C2–C6); 22.84 (Cβ); 21.14 (Cγ); 15.61 (CH$_3$).

Example 13

N-[4-(2-thienyl)-tetrahydro-4H-thiopyran-4-yl]-3-hydroxy piperidine

Stage 13a: 4-(3-hydroxypiperidino)-tetrahydro-4H-thiopyran-4-carbonitrile 3-hydroxy-piperidine hydrochloride (6.5 g, 47.3 mmoles) in 30 ml of water is introduced into a 100 ml two-necked flask. Potassium cyanide (1.85 g, 35.5 mmoles) is added and tetrahydro-4H-thiopyran-4-one (2.7 g, 23.6 mmoles) is introduced dropwise. The pH of the medium is adjusted to 11 with a few drops of soda (10%). After 24 hours under agitation at ambient temperature, extraction with ether (3×80 ml) is carried out, the combined organic phases are washed with water (100 ml), dried over Na$_2$SO$_4$, filtered and concentrated to dryness. In this way, a colourless oil is obtained (3.9 g, 17.2 mmoles).

NMR $^{13}$C: 117.87 (CN); 66.25 (Cβ); 59.19 (C4); 53.20; 45.96 (Cα'); 33.94 (C3–C5); 31.79 (Cγ); 22.70 (C2–C6); 21.90 ( (Cβ').

Stage 13b: N-[4-(2-thienyl)-tetrahydro-4H-thiopyran-4-yl]-3-hydroxy piperidine 2-thienylmagnesium bromide is prepared under nitrogen starting from magnesium (1.3 g, 53.2 mmoles), 2-bromothiophene (8.7 g, 53.2 mmoles) and 100 ml of anhydrous ether followed by heating at 45° C. for 3 hours, then the aminonitrile obtained in Stage 13a (3 g, 13.3 mmoles) dissolved in ether is added at ambient temperature. The reaction medium is heated for 20 hours under reflux. After treatment of the reaction, 2.3 g of a brown oil is obtained which is chromatographed on silica eluting with an EP/EA (30/70) mixture. In this way, a white solid is obtained (42%).

M.p.=84–87° C. NMR $^{13}$C: 145.82 (C2'); 126.71 to 123.13 (C3' to C5'); 66.83 (Cβ); 58.23 (C4); 52.52 (Cα); 45.89 (Cα'); 36.40 (C3–C5); 32.18 (Cγ); 23.40 (C2–C6); 22.36 (Cβ').

Characteristics of the corresponding hydrochloride:

M.p.=169–172° C. NMR $^{13}$C: 134.26 (C2'); 130.78 to 128.29 (C3' to C5'); 69.69 (C4); 63.75 (Cβ); 51.31 (Cα); 46.18 (Cα'); 34.10 (C3–C5); 31.22 (Cγ); 25.28 (C2–C6); 20.38 (Cβ').

Example 14

N-[4-(2-thienyl)-tetrahydro-4H-thiopyran-4-yl]-4-hydroxy piperidine

Stage 14a: 4-(4-hydroxypiperidino)-tetrahydro-4H-thiopyran-4-carbonitrile

It is prepared from MgSO$_4$ (7.2 g, 60 mmoles), DMA (2.62 g, 30 mmoles), 4-hydroxy-piperidine (3.03 g, 20 mmoles), tetrahydro-4H-thiopyran-4-one (2.32 g, 20 mmoles) and acetone cyanhydrin (1.7 g, 20 mmoles). After treatment of the reaction, a white solid is obtained (4.7 g) which is crystallized from anhydrous ether. In this way, white crystals are obtained (3.6 g, 79%). M.p.=79–81° C.

NMR $^{13}$C: 118.28 (CN); 66.67 (Cγ); 59.42 (C4); 43.87 (Cα); 33.96 (C3–C5*); 34.33 (Cβ*); 22.91 (C2–C6).

Stage 14b: N-[4-(2-thienyl)-tetrahydro-4H-thiopyran-4-yl]-4-hydroxy piperidine 2-thienylmagnesium bromide is prepared under nitrogen from magnesium (0.45 g, 18.5 mmoles), 2-bromothiophene (3 g, 18.5 mmoles) and 50 ml of anhydrous ether followed by heating at 45° C. for 3 hours, then the aminonitrile obtained in Stage 14a (1.4 g, 6.2 mmoles) dissolved in ether is added at ambient temperature. The reaction medium is heated for 20 hours under reflux. After treatment of the reaction, 1.5 g of a brown solid is obtained which is chromatographed on alumina eluting with anhydrous ether. In this way, a white solid is obtained (0.85 g,49%).

M.p.=145–148° C. NMR $^{13}$C(D$_2$O): 146.19 (C2'); 126.07 to 122.98 (C3' to C5'); 68.18 (Cγ); 58.24 (C4); 42.67 (Cα); 36.92 (C3–C5*); 35.19(Cβ*); 23.40 (C2–C6).

Characteristics of the corresponding hydrochloride:

M.p.=182–185° C. NMR $^{13}$C: 136.63 (C2'); 134.19 to 130.98 (C3' to C5'); 72.05 (C4); 67.53 (Cγ); 48.04 (Cα); 36.71 (C3–C5); 33.87 (Cβ); 27.45 (C2–C6).

Example 15

N-[1-(2-thienyl)-cyclohexan-1-yl]-4-hydroxy-3-methyl piperidine

Stage 15a: ethyl N-benzoyl-4-piperidone-3-carboxylate

Benzamide (12.1 g, 0.1 mmoles) in 200 ml of toluene is introduced into a 250 ml three-necked flask of 250 ml under nitrogen, and sodium hydride (4 g, 0.1 moles) is added, followed by heating for one hour under reflux, then cooling down to 0° C., and ethyl acrylate (32.6 ml, 0.3 moles) is poured rapidly. The reaction medium is agitated for 24 hours at 60° C., followed by cooling down to 0° C., and 100 ml of ice-cooled water is added. After ½ hour under agitation, the two phases are decanted and the aqueous phase is washed with 50 ml of ether. The aqueous phase is acidified to pH 3 then extracted with dichloromethane (3×50 ml). The combined organic phases are dried over Na$_2$SO$_4$ and concentrated to dryness. In this way, a yellow oil is obtained which is chromatographed on silica eluting rapidly with anhydrous ether. In this way, a slightly redColoured oil is obtained (9.4 g, 34%) having traces of benzamide.

NMR $^{13}$C: 201.63 (C4); 197.5 (C4enol); 170.89 and 170.4(CO amide and ester); 135.25 to 126.87 (Caromatics); 95.73 (C3enol); 61.4 and 60.46 (CH$_2$ enol and ketone); 56.01 (C3); 41.05 (C6); 34.55 (C2); 28.78 (C5); 13.95 and 13.76 (CH$_3$ enol and ketone).

Stage 15b: ethyl N-benzoyl-4-piperidone-3-carboxylate

The mixture constituted by the keto-ester in Stage 15a (9.3 g, 33.8 mmoles) and sodium hydride (1.35 g, 34 mmoles) in 50 ml of dimethoxyethane is heated under reflux for 2 hours under agitation followed by cooling down to 0° C., and methyl iodide (5.2 ml, 84 mmoles) is added. The reaction medium is heated fog 40 hours at 60° C. followed by concentrating to dryness, and the residue is taken up in water (100 ml). Extraction with dichloromethane (3×50 ml) is carried out, the combined organic phases are washed with 50 ml of NaOH (5%), 50 ml of HCl (5%) and 50 ml of water, followed by drying over $Na_2SO_4$ and concentrating to dryness. The brown oil obtained (9.4 g) is chromatographed on silica eluting with anhydrous ether. A slightly yellow oil is obtained (7.7 g, 79%).

NMR $^{13}$C: 203.89 (C4); 170.54 (CO amide and ester); 134.76 to 126.87 (Caromatics); 61.56 (CH2Et); 57.11 (C3); 39.05 (C6); 17.15 ($CH_3$); 13.60 ($CH_3Et$).

Stage 15c: 3-methyl-4-piperidone hydrochloride

The compound of Stage 15b (7.7 g, 26.6 moles) is heated under reflux of an aqueous solution of HCL (6N) for 72 hours. The precipitate of benzoic acid formed is filtered, the aqueous phase is extracted with ether (3×50 ml) and the aqueous phase concentrated to dryness. The brown solid obtained is crystallized from ethanol and in this way white crystals are obtained (2.85 g, 72%). M.p.=180–182° C.

NMR $^{13}$C: 210.38 (C4); 54.58 (C2); 47.67 (C6); 47.01 (C3); 42.98 (C5); 11.18 ($CH_3$).

Stage 15d: 3-methyl-4-piperidol

The compound of Stage 15c (2.85 g, 19 mmoles) and 30 ml of methanol are introduced into a 100 ml three-necked flask. 7.6 ml of a soda solution (5%) is introduced dropwise. After ½ hour under agitation, a solution of sodium borohydride (2.46 g, 6.5 mmoles) in 30 ml of methanol is poured in. The reaction medium is agitate d for 4 hours at ambient temperature. The medium is cooled down to 0° C., a few drops of an HCl solution are added, followed by concentrating to dryness. The yellow solid obtained is taken up in warm ethanol and the product is precipitated by adding a few drops of ether. The precipitate is filtered and in this way a white solid (1.9 g, 87%) is obtained. M.p.=169–1709C.

NMR $^{13}$C ($D_2O$):
Majority diastereoisomer: 73.24 (C4); 50.75 (C2); 45.69 (C6); 38.45 (C3); 32.92 (C5);16.8 ($CH_3$).
Minority diastereoisomer: 67.94 (C4); 46.97 (C2); 41.32 (C6); 34.89 (C3); 31.29 (C5);16.47 ($CH_3$).

Stage 15e: 3-(4-hydroxy-3-metlyl-piperidino)-cyclohexan-1-carbonitrile

The compound of Stage 15d (0.8 g, 7 mmoles) in 10 ml of water is introduced into a 50 ml two-necked flask. Cyclohexanone (2.7 g, 23.6 mmoles) and a few drops of HCl are added in order to adjust the pH to 3. Potassium cyanide (0.47 g, 7.3 mmoles) is then added. The pH of the medium is then close to 11. After 24 hours under agitation at ambient temperature, extraction with dichloromethane is carried out, followed by drying over $Na_2SO_4$, filtering and concentrating to dryness. In this way, a colourless oil is obtained (1.43 g, 6.4 mmoles) representing only one of the two diastereoisomers.

NMR $^{13}$C: 118.97 (CN); 73.69 (Cγ); 60.57 (C1); 52.43 (Cα); 45.37 (Cα'); 38.57 (Cβ); 34.22 (Cβ'*); 33.98 (C2–C6*); 33.87 (C4*); 21.91 (C3–C5); 15.61 ($CH_3$).

Stage 15f: N-[1-(2-thienyl)-cyclohexan-1-yl]-4-hydroxy-3-methyl piperidine 2-thienylmagnesium bromide is prepared under nitrogen from magnesium (0.38 g, 15.7 mmoles), 2-bromothiophene (2.57 g, 15.7 mmoles) and 60 ml of anhydrous ether. The reaction medium is heated at 45° C. for 3 hours, then the aminonitrile obtained in Stage 15e (0.7 g, 3.15 mmoles) dissolved in THF is added at ambient temperature. The reaction medium is heated for 20 hours under reflux. After treatment of the reaction, a brown oil is obtained which is chromatographed on alumina eluting with anhydrous ether. In this way, a white solid is obtained (0.48 g, 54%).

NMR $^{13}$C: 146.14 (C2'); 125.86 to 122.61 (C3' to C5'); 74.76 (Cγ); 59.34 (C1); 51.17 (Cα); 43.98 (Cα'); 39.36 (Cβ); 36.0 (C3–C5); 25.85 (C4*); 21.96 (C3–C5*); 15.75 ($CH_3$).

Characteristics of the corresponding hydrochloride:

NMR $^{13}$C: 135.09 (C2'); 129.98 to 127.55 (C3' to C5'); 70.60 (Cγ); 69.00 (C1); 50.59 (Cα); 45.30 (Cα'); 35.37 (Cβ); 32.80 (C3–C5); 30.77 (C2–C6); 23.43 (C4); 22.53 (C3–C5); 15.06 ($CH_3$).

Example 16

N-[1-(2-benzothiophenyl)-cyclohexan-1-yl]-4-hydroxy-3-methyl piperidine

The aminonitrile of Stage 15e (0.7 g, 3.15 mmoles) dissolved in 50 ml of anhydrous ether is introduced dropwise into a 2-benzothiophenylmagnesium bromide solution (15.75 mmoles). The reaction medium is heated under reflux of the ether for 16 hours. After the usual treatment, a yellow oil (0.85 g) is obtained which is chromatographed on alumina eluting with an EP/EA (20/80) mixture. In this way, a white solid is obtained (0.74 g, 71%).

M.p.=120–122° C. NMR $^{13}$C: 147.60 (C2'); 139.44 (C7'a); 138.64 (C3'a); 123.77 to 120.44 (C3' to C7'); 74.89 (Cγ); 59.98 (C1); 51.29 (Cγ); 44.16 (Cα'); 39.55 (Cβ); 33.84 (C2–C6); 35.27 (Cβ'); 25.86 (C4); 22.14 (C3–C5); 15.85 ($CH_3$).

Characteristics of the corresponding hydrochloride:

M.p.=170–172° C. NMR $^{13}$C: 139.60 (C2'); 139.02 (C7' and C3'a); 126.16 to 120.02 (C3' to C7'); 71.85 (Cγ): 65.66 (C1); 51.33 (Cα); 45.66 (Cα'); 36.54 (Cβ); 33.58 (C2–C6); 31.99 (Cβ'); 24.12 (C4); 22.80 (C3–C5); 15.54 ($CH_3$).

Example 17

N-ethyl-1-(2-thienyl)-cyclohexylamine

Stage 17a: 1-(2-thienyl)-cyclohexanol 2-thienylmagnesium bromide is prepared under nitrogen from magnesium (2.92 g, 120 mmoles), 2-bromothiophene (19.6 g, 120 mmoles) and 200 ml of anhydrous ether. The reaction medium is heated at 45° C. for 3 hours, then cyclohexanone (7.84 g, 80 mmoles) dissolved in ether is added at ambient temperature. The reaction medium is heated for 16 hours under reflux. After cooling down, the reaction medium is poured into 100 ml of a saturated aqueous solution of $NH_4Cl$, followed by agitation for ½ hour in order to destroy the magnesium complex, decanting and the aqueous phase is extracted with ether (3×50 ml). An acid-base extraction is carried out with an aqueous HCl solution at 15% (3×50 ml) which is then neutralised by $NH_4OH$ (25%). After extraction with ether (3×50 ml), the combined organic phases are washed with water until neutralised, dried over $Na_2SO_4$, filtered and concentrated to dryness. The brown oil obtained is chromatographed on silica eluting with an EP/EA (70/30) mixture. In this way, a slightly yellow limpid oil is obtained (12.1 g, 83%)

NMR $^{13}$C: 153.52 (C2'); 128.38 to 121.78 (C3' to C5'); 71.78 (C1); 39.73 (C2–C6); 25.2 (C4); 22.15 (C3–C5).

Stage 17b: 1-(2-thienyl)-cyclohexylazide

Trichloracetic acid (31.9 g, 195 mmoles) is dissolved in chloroform (200 ml). Sodium azide (8.45 g, 130 mmoles) is added and the medium is cooled down to 10° C. The alcohol obtained in Stage 17a (11.8 g, 65 mmoles) dissolved in chloroform (50 ml) is added dropwise. The reaction medium is agitated for 48 hours whilst maintaining the temperature at 10–12° C. A solution of ammonium hydroxide (10%) is then added until neutralisation, then the aqueous phase is extracted with dichloromethane (3×100 ml). The organic phase is washed with water (200 ml), dried over $Na_2SO_4$ and concentrated to dryness. In this way, a brown oil is obtained which is then used without further purification.

Stage 17c: 1-(2-thienyl)-cyclohexylamine

Lithium aluminium hydride (2.28 g, 60 mmoles) in 250 ml of THF is introduced into a 500 ml three-necked flask at 0° C. The azide obtained in the previous Stage 17b (13.5 g, 65 mmoles) dissolved in 30 ml of THF is introduced dropwise. The reaction medium is agitated for 24 hours at ambient temperature. The minimum amount of ammonium hydroxide (10%) is added very slowly in order to destroy the excess $LiAlH_4$, followed by filtration on celite, the precipitate is washed with dichloromethane (300 mnl) and concentrated to dryness. The oil obtained is taken up in ether and extracted with an HCl solution (10%) (3×100 ml). The aqueous phase is then neutralised with ammonium hydroxide (20%) and extracted with ether (3×100 ml). The organic phase is washed with water, dried over $MgSO_4$ and concentrated to dryness. The product obtained is purified by chromatography on alumina eluting with an EP/EA (60/40) mixture. In this way, a slightly yellow oil is obtained (8.1 g, 69%).

NMR $^{13}$C: 156.70 (C2'); 125.99 to 120.85 (C3' to C5'); 52.82 (C1); 40.39 (C2–C6); 25.17 (C4); 22.10 (C3–C5).

Stage 17d: N-acetoxy-1-(2-thienyl)-cyclohexylamine

The amine of Stage 17c (3 g, 16.6 mmoles) in pyridine (100 ml) is introduced into a 250 ml three-necked flask, and acetic anhydride (51 g, 50 mmoles) is added dropwise. After 4 hours under agitation at ambient temperature, 100 ml of an HCl solution (10%) is added and the product formed is extracted with ether (3×50 ml). The organic phase is washed with an HCl solution (10%) (2×80 ml), then with water (2×80 ml), dried over $MgSO_4$ and concentrated to dryness. In this way, a white solid is obtained (3.1 g, 84%).

NMR $^{13}$C: 169.44 (CO); 152.48 (C2'); 126.32 to 122.68 (C3' to C5'); 56.69 (C1); 37.32 (C2–C6); 25.22 (C4); 24.10 ($CH_3$); 22.11 (C3–C5).

Stage 17e: N-ethyl-1-(2-thienyl)-cyclohexylamine

Lithium aluminium hydride (0.51 g, 13.4 mmoles) in 80 ml of THF is introduced into a 500 ml three-necked flask at 0° C. The amine obtained in the previous Stage 17d (3 g, 13.4 mmoles) dissolved in 30 ml of THF is added dropwise. The reaction medium is agitated for 48 hours under reflux. The minimum amount of ammonium hydroxide (10%) is added very slowly in order to destroy the excess $LiAlH_4$, followed by filtering on celite, the precipitate is washed with dichloromethane (300 ml) and concentrated to dryness. The oil obtained is taken up in ether and extracted with an HCl solution (10%) (3×100 ml). The aqueous phase is then neutralised with ammonium hydroxide (20%) and extracted with ether (3×100 ml). The organic phase is washed with water, dried over $MgSO_4$ and concentrated to dryness. The product obtained is purified by chromatography on alumina eluting with an EP/EA (90/10) mixture. In this way, a colourless oil (1.7 g, 61%) is obtained.

NMR $^{13}$C: 154.18 (C2'); 125.81 to 122.52 (C3' to C5'); 56.60 (C1); 37.60 ($CH_2$); 35.74 (C2–C6); 25.51 (C4); 21.86 (C3–C5); 15.48 ($CH_3$).

Characteristics of the corresponding hydrochloride:

M.p.=214–216° C. NMR $^{13}$C: 139.53 (C2'); 128.49 to 126.65 (C3' to C5'); 62.12 (C1); 36.30 ($CH_2$); 34.46 (C2–C6); 24.30 (C4); 21.94 (C3–C5); 11.53 ($CH_3$).

Example 18

N-[1-(2-furyl)-cyclohexan-1-yl] piperidine

A solution of $MgBr_2$ is prepared from 1,2-dibromo-ethane (6.76 g, 36 mmol, 4 eq) and magnesium (0.88 g, 36 mmol, 4 eq) in ether (80 ml) under a nitrogen atmosphere. A 2-lithio-furan solution is prepared under nitrogen atmosphere by adding a 1.6M solution of n-butyl-lithium in hexane (28 ml, 45 mmol, 5 eq) dropwise to a mixture of furan (3.1 g, 45 mmol, 5 eq) and TMEDA (5.2 g, 45 mmol, 5 eq) in anhydrous ether (100 ml) at −20° C. The mixture is then taken to reflux for 2 hours, cooled down to ambient temperature and $MgBr_2$ in ether is added dropwise to the solution. A 1-piperidin-1-yl-cyclohexanecarbonitrile (1.7 g, 9 mmol, 1 eq) solution in ether is added dropwise at ambient temperature. The mixture is taken to reflux for 16 hours, cooled down to ambient temperature, then treated in the following manner: the mixture is poured gently into an ice-cooled saturated solution of $NH_4Cl$, agitated for 30 minutes, extracted with ether; the ethereal phases are combined, then extracted three times with 10% HCl, and 20% $NH_4OH$ is added to the aqueous phase until neutrality. The aqueous phase is extracted with ether, the organic phase is washed with water, dried over $Na_2SO_4$, filtered and concentrated under vacuum. The crude product is purified by chromatography on alumina with $CH_2Cl_2$ as eluent in order to produce an oil (1.7 g, 76%).

NMR $^{13}$C: 146.46 (C2'); 143.0 (C5'); 113.7 (C3'); 110.7 (C4'); 67.6 (C4); 47.0 (Cα); 29.8 (C3–C5); 23.4 (C1); 22.5 (C2–C6); 22.3 (Cβ); 21.7 (Cγ).

The corresponding hydrochloride is obtained in the form of a white solid. M.p.=166–167° C.

Example 19

N-[4-(2-thienyl)-tetrahydro-4H-thiopyran-4-yl] piperidine

Example 20

N-[4-(2-thienyl)-tetrahydro-4H-pyran-4-yl] piperidine

Example 21

N-[3-(2-thienyl)-tetrahydro-4H-thiopyran-3-yl] piperidine

Example 22

N-[1-(2-thienyl)-cyclohexan-1-yl]-3-methyl piperidine

The compounds corresponding to Examples 19 and 20 are described in Eur. J. Med. Chem. (1996) 31, pp 488–495. The compounds corresponding to Examples 21 and 22 are described in Arch. Pharm. (1987) vol. 320, no. 4 pp 348–361 and Eur. J. Med. Chem. (1995) 30, pp 463–470 respectively.

Using the process described above, the following compounds, which also form part of the invention, can also be prepared:

| Example | X | Y | Z | R4 | R₁R₂N— | Ar |
|---------|---|---|---|-----|--------|-----|
| A | C | S | C | H | 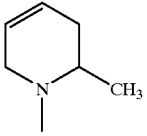 | 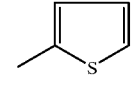 |
| B | C | S | C | 5-CH₃ | Et₂N— | 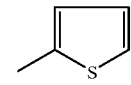 |
| C | C | O | C | H | 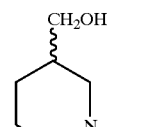 | 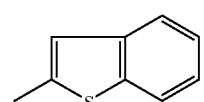 |
| D | S | C | S | H | 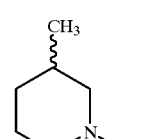 | 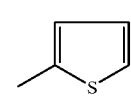 |
| E | C | O | C | H | 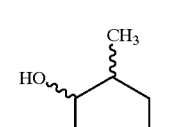 |  |
| F | S | C | C | H | 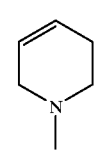 | 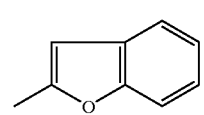 |
| G | C | O | C | H | 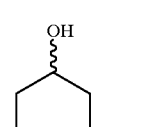 |  |
| H | C | O | C | H | EtMeN— | 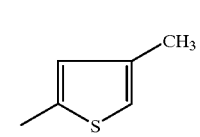 |
| I | C | S | C | 3-CH₃ | 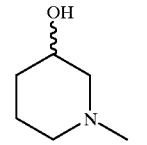 | 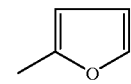 |
| J | C | O | C | H | 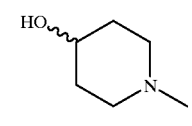 | 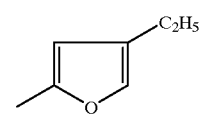 |

-continued

| Example | X | Y | Z | R4 | R₁R₂N— | Ar |
|---------|---|---|---|----|--------|----|
| K | C | O | C | H | 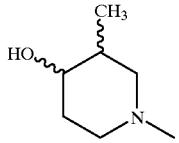 | 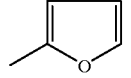 |

Pharmacological Study of the Compounds of the Invention

Principle of the affinity measurements in vitro

The affinity of the compounds for their potential bond site, can be evaluated by quantifying their ability to displace a specific tritiated label of a given site. The bond experiences are carried out by competition between the molecule to be tested and the appropriate radioligand on a membrane preparation rich in sites to be studied. The concentration of the derivative tested which inhibits 50% of the bond of the radioligand to the receptor is called $IC_{50}$.

For the $PCP_1$ sites, the tritiated label used is [³H]TCP and the tests are carried out on membrane preparations originating from anterior cerebrum homogenates of rats.

For the experimental conditions and membrane preparation techniques used, reference can be made to the literature (Brain Res., 378, 133–141 (1986); Eur. J. Pharm., 81, 531–542 (1982)).

For low affinity sites, the monosite treatment used led to incoherent results. The experimental data have therefore been reprocessed using non-linear regression (Marquardt-Levenberg algorithm) with Sigma Plot software (Jandel) according to a model with two noted sites of interaction $PCP_2$ and $PCP_3$. This processing proves to be more suitable than a monosite treatment (Student test: p<0.05) over a set of 3 to 4 experiments for each compound tested. Over all the experiments, the two site populations are found in a relative proportion to 68.0% (±1.5) for the $PCP_2$ sites and 31.2% (±1.5) for the $PCP_3$ sites.

For the $PCP_2$ and $PCP_3$ sites, the preparation originates from rat cerebella. Not having a specific label, only [³H]TCP can be used. A more significant concentration of tritiated ligand (2.5 nM versus 1 nM in the cortex) is used to ensure that all the $PCP_2$ and $PCP_3$ sites are occupied. The $IC_{50}$ values are presented in Table 1 below.

Percentage inhibition on PCP receptors:

The tritiated label used is [³H]TCP and the tests are carried out on membrane preparations originating from cerebral cortex of a rat (Brain Res., 378, 133–141 (1986).

| Compound (10 µM) | % inhibition |
|------------------|--------------|
| Ex 9  | 96 |
| Ex 10 | 18 |

TABLE 1

|  | cortex 1 site | | | cerebellum 2 sites | | | | |
|---|---|---|---|---|---|---|---|---|
| Compound | $IC_{50}$ (nM) | nH | n | $IC_{50}$ (nM) | $PCP_2$ (%) | $IC_{50}$ (nM) | $PCP_3$ (%) | n |
| TCP | — | — | — | 59 | 72.6 | 3716 | 29.8 | 5 |
| Ex 1 (majority) | 17233 | 0.94 | 3 | — | — | — | — | — |
| Ex 1 (minority) | 26.8 | 0.89 | 3 | 1355 | 62.8 | 17.6 | 34.7 | 4 |
| Ex 2 | 132 | 1.14 | 3 | 265 | 69.1 | 2850 | 31.6 | 3 |
| Ex 4 | 24 | 0.84 | 3 | 53.2 | 66.3 | 2076 | 34.6 | 4 |
| Ex 5 | >100 µM | — | 3 | >100 µM | 66.2 | 581 | 32.2 | 3 |
| Ex 6 | >100 µM | — | 3 | >100 µM | 55.6 | 280 | 39.4 | 3 |
| Ex 7 | 82825 | 0.73 | 4 | 84000 | 57.8 | 639 | 40.7 | 3 |
| Ex 8 | 28.4 | 0.96 | 3 | 2240 | 69 | 12.4 | 31 | 3 |
| Ex 9 | 133 | 0.87 | 3 | 1015 | 68.3 | 13.8 | 32.3 | 5 |
| Ex 10 | 27467 | 0.9 | 3 | 26633 | 65.0 | 59.1 | 33.4 | 3 |
| Ex 11 | 462 | 0.97 | 3 | 532 | 83 | >100 µM | 15.3 | 3 |
| Ex 12 | 77.8 | 0.93 | 3 | 772 | 76.4 | 5.4 | 21.8 | 4 |
| Ex 17 | 20.9 | 0.77 | 3 | 55 | 56.6 | 47600 | 44.6 | 3 |
| Ex 18 | 7.8 | 0.83 | 3 | 187 | 66.3 | 5.6 | 30.7 | 3 |
| Ex 19 | 71.6 | 1.05 | 3 | 586 | 75.2 | 8.5 | 25.2 | 3 |
| Ex 20 | 1223 | 0.98 | 3 | 5840 | 80.3 | 35 | 15.5 | 3 |
| Ex 21 | 73.4 | 1.00 | 3 | 659 | 77.8 | 8.0 | 23.4 | 3 |
| Ex 22 (±) | 5.5 | 1.09 | 3 | 47.3 | 68.5 | 1450 | 33.7 | 3 |
| (+) | 5.2 | 1.04 |  | 28.3 | 52.5 | 808 | 51.0 |  |
| (−) | 158 | 1.08 |  | — | — | — | — |  |

What is claimed is:

1. A compound selected from the group consisting of all racemic, enantiomeric ad diastereoisomeric forms of a compound of the formula

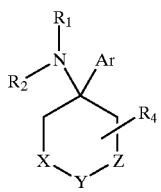

wherein Ar is selected from the group consisting of monocyclic, carbocyclic and heterocyclic aryl of 5 to 6 ring members or of condensed rings unsubstituted or substituted with at least one member of the group consisting of a) alkyl, alkenyl, alkynyl, alkoxy, alkylthio, haloalkyl and hydroxyalkyl of up to 6 carbon atoms and b) halogen, —OH, —CN, —NO$_2$, —NH$_2$ mono and dialkylamino of 1 to 6 alkyl carbon atoms, carboxy, salified carboxy and carboxy esterified with an alkanol of 1 to 6 carbon atoms, R$_1$ and R$_2$ are individually hydrogen or alkyl of up to 6 carbon atoms unsubstituted or substituted with at least one member of the group consisting of —OH, —CN, —NO$_2$, carboxy, salified carboxy and carboxy esterified with an alkanol of 1 to 6 carbon atoms or R$_1$ and R$_2$ together with the nitrogen to which they are attached form

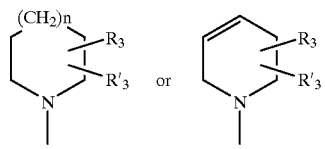

n is an integer from 0 to 2, R$_3$, R'$_3$ and R$_4$ are individually selected from the group consisting of a) hydrogen, halogen, —OH, —CN, —NO$_2$, carboxy, salified carboxy, carboxy esterified with an alkanol of 1 to 6 carbon atoms and b) alkyl, alkenyl, alkynyl, alkoxy, alkylthio, haloalkyl and hydroxyalkyl of up to 6 carbon atoms, and one of X, Y and Z is sulfur or oxygen and the other two are methylene with the exception of the compounds when R$_3$, R'$_3$ and R$_4$ are all hydrogen, 1) Ar is phenyl or 2-thienyl, R$_1$ and R$_2$ with the nitrogen form pyrrolidino and one of X, Y and Z is oxygen, or 2) R$_1$ and R$_2$ with the nitrogen form piperidino, Ar is phenyl, thienyl or benzothienyl, Y is sulfur and X and Z are methylene, 3) R$_1$ and R with the nitrogen form piperidino, Y is oxygen, X and Z are methylene and Ar is selected from the group consisting of phenyl, methoxyphenyl, benzothienyl and 2-thienyl, 4) R$_1$ and R$_2$ with the nitrogen form piperidino, Ar is phenyl, methoxyphenyl or 2-thienyl, one of X or Z is oxygen and the other and Y are methylene, 5) R$_1$ and R$_2$ with the nitrogen form piperidino, Ar is phenyl or 2-thienyl, one of X and Z is sulfur and the other and Y are methylene, 6) R$_1$ and R$_2$ with nitrogen form pyrrolidino, Ar is 2-thienyl, one of X or Z is sulfur and the other and Y are methylene, 7) R$_1$ and R$_2$ with the nitrogen form ethylamino or pyrrolidino, Ar is phenyl, Y is sulfur and X and Z are methylene or 8)
— N-[1-(2-thienyl)-cyclohexan-1-yl]-3-hydroxymethyl-piperidine,
— N-[1-(2-thienyl)-cyclohexan-1-yl]-4-hydroxy-3-methyl piperidine,
— N-[1-(2-benzothiophenyl)-cyclohexan-1-yl]-4-hydroxy-3-methyl piperidine,
— N-[1-(2-thienyl)-cyclohexan-1-yl]-3-methyl-piperidine,
— N-ethyl-1-(2-thienyl)-cyclohexylamine, or
— N-[1-(2-furyl)-cyclohexan-1-yl] piperidine, and their non-toxic,
pharmaceutically acceptable salts with bases and acids.

2. A compound of claim 1 wherein R$_1$ and R$_2$ are individually hydrogen or alkyl of 1 to 6 carbon atoms or together with the nitrogen form

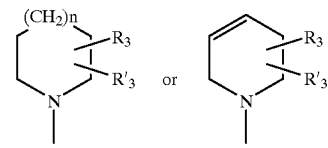

and R$_3$ and R'$_3$ are individually selected from the group consisting of hydrogen, —OH and alkyl and hydroxyalkyl of 1 to 6 carbon atoms and Ar is an heterocyclic aryl, monocyclic with 5 members or constituted by two condensed rings and unsubstituted or substituted by at least one alkyl or alkylene.

3. A compound of claim 1 wherein Ar is selected from the group consisting of thienyl, furyl, benzothienyl and benzofuryl, all unsubstituted or substituted with at least one member of the group consisting of methyl, ethyl, propyl and alkyl, R$_1$ and R$_2$ are individually hydrogen or methyl or ethyl or with the nitrogen atom form

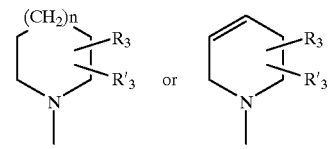

wherein R$_3$ and R'$_3$ are individually selected from the group consisting of hydrogen, —OH, hydroxymethyl, methyl, ethyl and hydroxyethyl.

4. As medicaments, the compounds of formula I as defined in claim 1, as well as the addition salts with mineral or organic acids or pharmaceutically acceptable mineral or organic bases of said compounds of formula I.

5. As medicaments, the compounds of formula I$_A$ as defined in claim 2, as well as the addition salts with pharmaceutically acceptable mineral or organic acids or mineral or organic bases of said compounds of formula I$_A$.

6. Pharmaceutical compositions containing, as active ingredient, at least one of the medicaments as defined in claim 5.

7. A method of protecting central or peripheral nervous system cells against acute degeneration induced by accidents in warm-blooded animals comprising administering to warm-blooded animals an amount of a compound of the formula

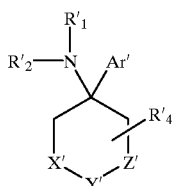

I'$_A$ wherein Ar' is monocyclic carbocyclic or heterocyclic aryl of 5 to 6 ring members or condensed rings, each unsubstituted or substituted with at least one member of the group consisting of a) halogen, —OH and alkyl, alkenyl, alkynyl, alkoxy, alkylthio, haloalkyl and hydroxy alkyl of up to 6 carbon atoms, b) carboxy, salified carboxy and carboxy esterified with an alkanol of up to 6 carbon atoms and c) —CN, —NO$_2$, —NH$_2$ and mono and dialkylamino of 1 to 6 alkyl carbon atoms, R'$_1$ and R'$_2$ are individually hydrogen or alkyl of 1 to 6 carbon atoms unsubstituted or substituted with at least one member of the group consisting of —OH, —CN, —NO$_2$, carboxy, salified carboxy and carboxy esterified with an alkanol of up to 6 carbon atoms or R'$_1$ and R'$_2$ taken with the nitrogen to which they are attached are:

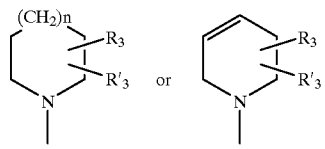

n is an integer from 0 to 2, R$_3$ and R'$_3$ are individually selected from the group consisting of a) hydrogen, halogen, —OH, —CN, —NO$_2$, carboxy, salified carboxy, carboxy esterified with an alkanol of up to 6 carbon atoms and b) alkyl, alkenyl, alkynyl, alkoxy, alkylthio, haloalkyl and hydroxyalkyl of up to 6 carbon atoms, R'$_4$ has the definition of R$_3$ or R'$_3$, one of X', Y' and Z' is oxygen or sulfur and the other two are methylene or all are methylene or a compound selected from the group
—N-[1-(2-thienyl)-cyclohexan-1-yl]-3-hydroxymethyl-piperidine,
—N-[1-(2-thienyl)-cyclohexan-1-yl]-4-hydroxy-3-methyl piperidine,
—N-[1-(2-benzothiophenyl)-cyclohexan-1-yl]-4-hydroxy-3-methyl piperidine or
—N-ethyl-1-(2-thienyl)-cyclohexylamine,
—N-[1-(2-furyl-cyclohexan-1-yl] piperidine,
—N-[1-(2-thienyl)-cyclohexan-1-yl]-3-methyl-piperidine,
in all possible racemic, enantiomeric and diastereolsomeric forms and its non-toxic, pharmaceutically acceptable addition salts sufficient to protect central and peripheral nervous system cells against acute degeneration caused by accidents.

8. The method of claim 7 wherein the compound is of formula I'$_A$ wherein
Ar' represents an heterocyclic aryl radical, monocyclic with 5 members or constituted by two condensed rings and optionally substituted by one or more identical or different alkyl or alkenyl radicals;
R'$_1$ and R'$_2$, identical or different, represent a hydrogen atom or an alkyl radical having at most 6 carbon atoms or R$_1$ and R$_2$ form with the nitrogen atom to which they are linked a

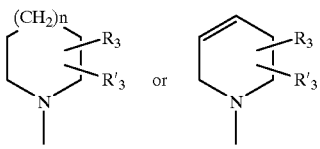

radical in which n is equal to 1 and R$_3$ and R'$_3$, identical or different, represent a hydrogen atom or a hydroxyl, alkyl or hydroxyalkyl radical having at most 6 carbon atoms.

9. The method of claim 7 wherein the compound is of formula I'$_A$ wherein
Ar' represents the thienyl, furyl, benzothienyl, benzofuryl radical and optionally substituted by one or more methyl, ethyl, propyl or allyl radicals;
R'$_1$ and R'$_2$ identical or different represent a hydrogen atom or a methyl or ethyl radical, or
R$_1$ and R$_2$ form with the nitrogen atom to which they are linked a

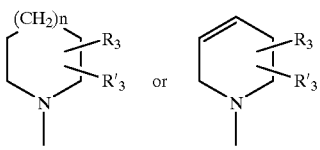

radical in which n is equal to 1 and R$_3$ and R'$_3$, identical or different, represent a hydrogen atom or a hydroxyl, hydroxymethyl, hydroxyethyl, methyl or ethyl radical, for the preparation of medicaments as defined above.

10. The method of claim 7 wherein the compound is selected from the group consisting of:
—N-[4-(2-thienyl)-3-methyl-tetrahydro-4H-thiopyran4-yl]-piperidine;
—N-[4-(2-thienyl)-tetrahydro-4H-thiopyran4-yl]-3-methyl-piperidine;
—N-[4-(2-benzothiophenyl)-tetrahydro-4H-thiopyran-4-yl]-3-methyl-piperidine;
—N-[4-(2-furyl)-tetrahydro-4H-thiopyran-4-yl]-piperidine;
—N-[4-(2-benzofuranyl)-tetrahydro-4H-thiopyran-4-yl]-piperidine;
—N-[4-(5-methyl-thiophen-2-yl)-tetrahydro-4H-thiopyran-4-yl]-piperidine;
—N-[4-(4-methyl-thiophen-2-yl)-tetrahydro-4H-thiopyran-4-yl]-piperidine;
—N-[4-(2-thienyl)-tetrahydro-4H-thiopyran-4-yl]-3-hydroxy piperidine;
—N-[4-(2-thienyl)-tetrahydro-4H-thiopyran-4-yl]-4-hydroxy piperidine.

11. A method of protecting central or peripheral nervous system cells against chronic degeneration induced by neurodegenerative diseases in warm-blooded animals comprising administering to warm-blooded animals an amount of a compound of the formula

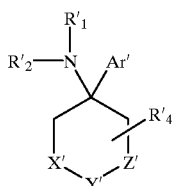

wherein Ar' is monocyclic carbocyclic or heterocyclic aryl of 5 to 6 ring members or condensed rings, each unsubstituted or substituted with at least one member of the group consisting of a) halogen, —OH and alkyl, alkenyl, alkynyl, alkoxy, alkylthio, haloalkyl and hydroxy alkyl of up to 6 carbon atoms, b) carboxy, salified carboxy and carboxy esterified with an alkanol of up to 6 carbon atoms and c) —CN, —NO$_2$, —NH$_2$ and mono and dialkylamino of 1 to 6 alkyl carbon atoms, R'$_1$ and R'$_2$ are individually hydrogen or alkyl of 1 to 6 carbon atoms unsubstituted or substituted with at least one member of the group consisting of —OH, —CN, —NO$_2$, carboxy, salified carboxy and carboxy esterified with an alkanol of up to 6 carbon atoms or R'$_1$ and R'$_2$ taken with the nitrogen to which they are attached are:

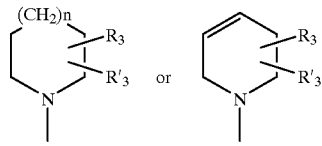

n is an integer from 0 to 2, R$_3$ and R'$_3$ are individually selected from the group consisting of a) hydrogen, halogen, —OH, —CN, —NO$_2$, carboxy, salified carboxy, carboxy esterified with an alkanol of up to 6 carbon atoms and b) alkyl, alkenyl, alkynyl, alkoxy, alkylthio, haloalkyl and hydroxyalkyl of up to 6 carbon atoms, R'$_4$ has the definition of R$_3$ or R'$_3$, one of X', Y' and Z' is oxygen or sulfur and the other two are methylene or all are methylene or a compound selected from the group
- —N-[1-(2-thienyl)-cyclohexan-1-yl]-3-hydroxymethyl-piperidine,
- —N-[1-(2-thienyl)-cyclohexan-1-yl]-4-hydroxy-3-methyl piperidine,
- —N-[1-(2-benzothiophenyl)-cyclohexan-1-yl]-4-hydroxy-3-methyl piperidine or
- —N-ethyl-1-(2-thienyl)-cyclohexylamine,
- —N-[1-(2-furyl)-cyclohexan-1-yl] piperidine,
- —N-[1-(2-thienyl)-cyclohexan-1-yl]-3-methyl-piperidine, in all possible racemic, enantiomeric and diastereoisomeric forms and its non-toxic, pharmaceutically acceptable addition salts sufficient to protect the central and peripheral nervous system cells against chronic degeneration induced by neurodegenerative diseases.

12. A method of treating a state of dependency on addictive drugs in warm-blooded animals comprising administering to warm-blooded animals an amount of a compound the formula

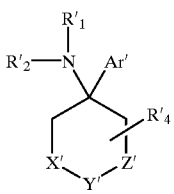

wherein Ar' is monocyclic carbocyclic or heterocyclic aryl of 5 to 6 ring members or condensed rings, each unsubstituted or substituted with at least one member of the group consisting of a) halogen, —OH and alkyl, alkenyl, alkynyl, alkoxy, alkylthio, haloalkyl and hydroxy alkyl of up to 6 carbon atoms, b) carboxy, salified carboxy and carboxy esterified with an alkanol of up to 6 carbon atoms and c) —CN, —NO$_2$, —NH$_2$ and mono and dialkylamino of 1 to 6 alkyl carbon atoms, R'$_1$ and R'$_2$ are individually hydrogen or alkyl of 1 to 6 carbon atoms unsubstituted or substituted with at least one member of the group consisting of —OH, —CN, —NO$_2$, carboxy, salified carboxy and carboxy esterified with an alkanol of up to 6 carbon atoms or R'$_1$ and R'$_2$ taken with the nitrogen to which they are attached are:

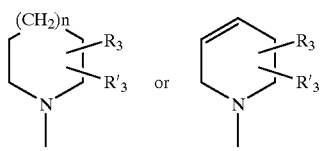

n is an integer from 0 to 2, R$_3$ and R'$_3$ are individually selected from the group consisting of a) hydrogen, halogen, —OH, —CN, —NO$_2$, carboxy, salified carboxy, carboxy esterified with an alkanol of up to 6 carbon atoms and b) alkyl, alkenyl, alkynyl, alkoxy, alkylthio, haloalkyl and hydroxyalkyl of up to 6 carbon atoms, R'$_4$ has the definition of R$_3$ or R'$_3$, one of X', Y' and Z' is oxygen or sulfur and the other two are methylene or all are methylene or a compound selected from the group
- —N-[1-(2-thienyl)-cyclohexan-1-yl]-3-hydroxymethyl-piperidine,
- —N-[1-(2-thienyl)-cyclohexan-1-yl]-4-hydroxy-3-methyl piperidine,
- —N-[1-(2-benzothiophenyl)-cyclohexan-1-yl]-4-hydroxy-3-methyl piperidine or
- —N-ethyl-1-(2-thienyl)-cyclohexylamine,
- —N-[1-(2-furyl)-cyclohexan-1-yl] piperidine,
- —N-[1-(2-thienyl)-cyclohexan-1-yl]-3-methyl-piperidine, in all possible racemic, enantiomeric and diastereoisomeric forms and its non-toxic, pharmaceutically acceptable addition salts sufficient to treat dependency on addictive drugs.

13. Preparation process for the compounds of general formula I as defined in claim 1,
characterized in that it comprises
the reaction of a compound of formula 1

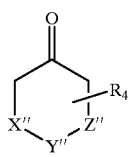

in which X", Y", Z" represent a sulphur or oxygen atom or a methylene radical, $R_4$ has the meaning indicated above, with a aryl magnesium halide of formula Ar—Mg—Hal in which Hal represents a halogen atom and Ar has the meaning indicated above, in order to obtain the compound of formula 2

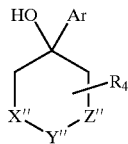

in which X", Y", Z", Ar and $R_4$ have the meanings indicated above, the conversion of the hydroxyl radical of the alcohol of formula 2 thus obtained, to the azide of formula 3

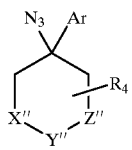

in which X", Y", Z", Ar and $R_4$ have the meaning indicated above, then the reduction of the azide of formula 3 to the primary amine of formula 4

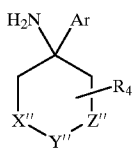

in which X", Y", Z", Ar and $R_4$ have the meanings given above;

and finally, if the desired compound of formula I is such that at least one of the $R_1$ or $R_2$ radicals is different from the hydrogen atom or $R_1$ and $R_2$ form a ring with the nitrogen atom to which they are linked, the treatment of this compound of formula 4 in order to obtain the compound of formula I which is converted into the salt if desired.

14. A process for the preparation of a compound of claim 1 comprising reacting a compound of formula I

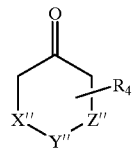

in which X", Y", Z" and $R_4$ have the meaning of claim 1 in anhydrous medium, with a compound of the formula $R_1R_2NH$ in which $R_1$ and $R_2$ have the meanings of claim 1 and a cyanide ion donor compound to obtain the compound of formula 5

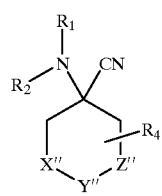

in which X", Y", Z" and $R_1$ and $R_2$ have the meanings indicated above and reacting the compound of formula 5 with an aryl magnesium halide of the formula Ar—Mg—Hal in which Ar has the meaning of claim 1 and Hal is halogen to obtain the compound of formula I.

15. A compound of claim 1 selected from the group consisting of:
—N-[4-(2-thienyl)-3-methyl-tetrahydro-4H-thiopyran-4-yl]-piperidine;
—N-[4-(2-thienyl)-tetrahydro-4H-thiopyran-4-yl]-3-methyl-piperidine;
—N-[4-(2-benzothiophenyl)-tetrahydro-4H-thiopyran-4-yl]-3-methyl-piperidine;
—N-[4-(2-furyl)-tetrahydro-4H-thiopyran-4-yl]-piperidine;
—N-[4-(2-benzofuranyl)-tetrahydro-4H-thiopyran-4-yl]-piperidine;
—N-[4-(5-methyl-thiophen-2-yl)-tetrahydro-4H-thiopyran-4-yl]-piperidine;
—N-[4-methyl-thiophen-2-yl)-tetrahydro-4H-thiopyran-4-yl]-piperidine;
—N-[4-(2-thienyl)-tetrahydro-4H-thiopyran-4-yl]-3-hydroxy piperidine or
—N-[4-(2-thienyl)-tetrahydro-4H-thiopyran-4-yl]-4-hydroxy piperidine.

* * * * *